US008609655B2

(12) United States Patent
Geibel et al.

(10) Patent No.: US 8,609,655 B2
(45) Date of Patent: Dec. 17, 2013

(54) CALCIMIMETIC COMPOUND FOR USE IN THE TREATMENT OF EPITHELIAL INJURY

(75) Inventors: John Peter Geibel, Branford, CT (US);
Steven C. Hebert, Plantation, FL (US);
Patricia R. Hebert, legal representative, Plantation, FL (US); David Martin, San Francisco, CA (US); Gordon Ng, Newbury Park, CA (US); William G. Richards, Thousand Oaks, CA (US); Joanne L. Viney, Westlake Village, CA (US)

(73) Assignee: Amgen Inc., Thousand Oaks, CA (US)

( * ) Notice: Subject to any disclaimer, the term of this patent is extended or adjusted under 35 U.S.C. 154(b) by 146 days.

(21) Appl. No.: 12/935,263

(22) PCT Filed: Mar. 27, 2009

(86) PCT No.: PCT/US2009/038659
§ 371 (c)(1),
(2), (4) Date: Feb. 25, 2011

(87) PCT Pub. No.: WO2009/121015
PCT Pub. Date: Oct. 1, 2009

(65) Prior Publication Data
US 2011/0144102 A1    Jun. 16, 2011

Related U.S. Application Data

(60) Provisional application No. 61/072,264, filed on Mar. 28, 2008.

(51) Int. Cl.
*A61K 31/5377* (2006.01)
*A61K 31/137* (2006.01)
*A61K 31/42* (2006.01)
*A61K 31/4418* (2006.01)
*A61P 17/02* (2006.01)
*A61P 1/00* (2006.01)

(52) U.S. Cl.
USPC ......... 514/233.8; 514/654; 514/378; 514/354

(58) Field of Classification Search
None
See application file for complete search history.

(56) References Cited

U.S. PATENT DOCUMENTS

| 5,763,569 A | 6/1998 | Brown et al. |
| 6,011,068 A | 1/2000 | Nemeth et al. |
| 6,031,003 A | 2/2000 | Nemeth et al. |

(Continued)

FOREIGN PATENT DOCUMENTS

| WO | WO 2007/027548 | * | 3/2007 |
| WO | WO-2007027548 | * | 3/2007 |

(Continued)

OTHER PUBLICATIONS

Velasco et al. "Successful treatment of calciphylaxis with cinacalcet-an alternative to parathyroidectomy", Nephrol. Dial. Transplant, 2006, vol. 21, 1999-2004.*

(Continued)

*Primary Examiner* — Ernst Arnold
*Assistant Examiner* — Jianfeng Song
(74) *Attorney, Agent, or Firm* — Olga Mekhovich

(57) ABSTRACT

This invention relates generally to the field of medicine and, more specifically, to methods for treating epithelial injury, in particular, due to ischemia, hypoxia, trauma, chemolytics or radiation exposure.

5 Claims, 8 Drawing Sheets

(56) References Cited

U.S. PATENT DOCUMENTS

| | | | |
|---|---|---|---|
| 6,211,244 B1 | 4/2001 | Van Wagenen et al. | |
| 6,908,935 B2 | 6/2005 | Kelly et al. | |
| 8,093,299 B2 * | 1/2012 | Geibel et al. | 514/650 |
| 2007/0249520 A1 | 10/2007 | Gore et al. | |

FOREIGN PATENT DOCUMENTS

| | | |
|---|---|---|
| WO | WO 2008/057282 | 5/2008 |
| WO | WO 2008/075173 | 6/2008 |
| WO | WO 2008/121386 | 10/2008 |

OTHER PUBLICATIONS

Field, "Intestinal ion transport and the pathophysiology of diarrhea", J. Clin. Invest. 2003, 111, 931-943.*

Howes, "Topical use of streptomycin in wounds", American Journal of Medicine, 1947, vol. 2, 449-456.*

Nemeth et al. "Calcimimetic Compounds: a Direct Approach to Controlling Plasma Levels of Parathyroid Hormone in Hyperparathyroidism", TEM, 1999, vol. 10, 66-71.*

Osborne et al. An electron microscopic investigation of time-related changes in the intestine of neonatal mice infected with murine rotavirus. J. Pediat. Gastroenterol. Nutr., Mar./Apr. 1998, 236-248.*

Ismail et al., "Proximal calciphylaxis treated with calcimimetic 'cinacalcet'", Nephrol Dial Transplant 23:1, 387-389, 2008.

Almy et al., "Chronic and recurrent diarrhea" Disease-a-Month, vol. 1, No. 10, 2-32, 1955.

Reed et al., "Cutaneous tissue repair: practical implications of current knowledge. II" Journal of the American Academy of Dermatology, vol. 13, No. 6, 1985.

Mikulec et al., "Diltiazem spares corneal A[delta] mechano and C fiber cold receptors and preserves epithelial wound healing", Database Embase, Elsevier Science Publishers, vol. 14, No. 5, 490-496, 1995.

Howes et al., "Topical use of streptomycin in wounds", American Journal of Medicine, vol. 2, No. 5, 1947.

Resta-Lenert et al., "Antibiotics versus probiotic treatments in the mdrla-/-mouse model of colitis", Faseb Journal Conf—Experimental Biology 2005 Meeting/35th International Congress of Physiological Sciences, vol. 20, No. 5, A1270, 2006.

Cheng et al., "Extracellular polyamines regulate fluid secretion in rat colonic crypts-sensing receptor", Gastroenterology, vol. 126, No. 1, 157, 2004.

Takeuchi Koji et al., "Effect of (S)-4-(1-(5-chloro-2-(4-fluorophenyoxy)benzamido)ethyl) benzoic acid (CJ-42794), a selective antagonist of prostaglandin E receptor subtype 4, on ulcerogenic and healing responses in rat gastrointestinal mucosa" Journal of Pharmacology and Experimental Therapeutics, vol. 322, No. 3, 903-912, 2007.

Ovbiagele et al., "Are elevated admission calcium levels associated with better outcomes after ischemic stroke?", Neurology, 67, 170-173, 2006.

Zhang et al., "Involvement of calcium-sensing receptor in ischemia-reperfusion-induced apoptosis in rat cardiomyocytes", Biochemical and Biophysical Researach Communications, 347, 872-881, 2006.

Buemi et al., "Cinaclacet modifies the pH of solutions in vitro: possible implications for gastro-intestinal side effects in vivo", Nephrology Dialysis Transplantation, vol. 22, No. 8, 2409-2411, 2007.

Orlando et al., "Mechanisms of epithelial injury and inflammation in gastrointestinal diseases", Reviews in Gastroenterological Disorders, Vo., 2, No. Suppl. 02, 502, 2002.

Tesfamariam et al., "Endothelial injury in the initiation and progression of vascular disorders", Vascular Pharmacology, vol. 46, No. 4, 229-237, 2007.

* cited by examiner

CALCIMIMETIC COMPOUND FOR USE IN THE TREATMENT OF EPITHELIAL INJURY

FIELD OF THE INVENTION

This invention relates generally to the field of medicine and, more specifically, to methods for treating or preventing epithelial injury, in particular, due to ischemia, hypoxia, trauma, chemolytics or radiation exposure.

BACKGROUND OF THE INVENTION

The rapidly dividing intestinal epithelium is very sensitive to damage due to ischemia, chemotherapy or irradiation. The resulting epithelial injury leads to important metabolic and structural alterations in a variety of intestinal cells that can eventually cause cell destruction and death. Despite the fact that restitution of blood flow is necessary to limit the progression of cellular injury associated with ischemia, restoration of blood flow and oxygenation to the ischemic intestine can result in a paradoxical enhancement of tissue injury (reperfusion injury). Chemotherapeutic agents exert their cytoablative actions on rapidly proliferating cells via several different mechanisms, ultimately leading to cell cycle arrest and/or cellular apoptosis. The cytotoxic actions of chemolytics/chemotherapeutic agents are not tumor-specific. Gastrointestinal toxicity following the administration of chemolytics is characterized by severe mucositis, weight loss and systemic infection. Limitation in dose and treatment of chemolytic agents due to gastrointestinal (GI) toxicity impair the effectiveness of chemotherapy in susceptible patients.

The use of multimodality therapies that include radiation have become commonplace in treating many malignancies—about one half of patients with cancer receive radiation therapy as a component of their treatment. Modern techniques for tomographic localization and fractionation of radiation therapy have significantly reduced short-term and long-term gastrointestinal morbidity resulting from radiation therapy. Nevertheless, most patients experience GI symptoms associated with acute radiation therapy, such as diarrhea, abdominal pain, bloating, tenesmus, and bleeding. Chest pain, dysphagia, and odynopagia may be seen when the radiation fields involve the upper GI tract. Usually these symptoms resolve shortly after radiation treatment ends. However, up to one fourth of patients who receive radiation therapy also develop some form of chronic injury, defined as symptoms presenting more than three months after completion of therapy. Symptoms are usually evident within the first two years after initiation of therapy. However, some patients do not develop symptoms for years or even decades.

Exposure of the skin to ultraviolet (UV) light cans produce immediate as well as long-term effects. The predominant acute effects of exposure to UV light include sunburn and vitamin D synthesis. Chronic exposure to UV light can produce photodamaged skin which exhibits wrinkling blotchiness, telangiectasia and a roughened, weather-beaten appearance as well as the more serious consequence of the development of melanoma or nonmelanoma skin cancer. Although the risk of skin cancer does not correlate well with cumulative exposure to UV light, skin cancers are generally considered long-term sequela of exposure to UV light.

A cutaneous wound may take 12 to 18 months to fully repair and scarring is the result of an injury that causes an exaggerated healing response that interferes with proper wound healing. Scars may be result of wounds, burns, surgeries, accidents and may be caused by bacteria and skin conditions such as acne.

There is need for therapies that provide a treatment regimen that is effective in inhibiting epithelial injury related cell death and promoting cell survival.

SUMMARY OF THE INVENTION

The present invention provides methods for treating or preventing epithelial injury comprising administering to a subject in need thereof a therapeutically acceptable dose of a pharmaceutical composition comprising a calcimimetic and a pharmaceutically acceptable diluents or carrier. In one aspect, the epithelial injury is intestinal. In another aspect, the epithelial injury is cutaneous.

In one aspect, epithelial injury can be induced by hypoxia or ischemia. In another aspect, epithelial injury may be due to a chemolytic agent. In a further aspect, epithelial injury may be chemotherapy-induced cytotoxicity. In another aspect, epithelial injury may be induced by radiation. In another aspect, epithelial injury may be induced by toxins, infectious agents or chemical agents.

The present invention encompasses methods for alleviating epithelial injury by a pretreatment regimen comprising administering to a subject in need thereof a therapeutically effective amount of a calcimimetic compound. In one aspect, the pretreatment regimen comprises administering to a subject in need thereof a therapeutically effective amount of a calcimimetic compound up to three days before the epithelial injury. In another aspect, the methods of the invention can further comprise a post-treatment regimen.

The methods of the invention are described in more detail in Detailed Description.

The calcimimetic compounds useful in the methods of the present invention are described in detail in Detailed Description below.

In one aspect, the subject can be mammal. In one aspect, the subject can be human.

DETAILED DESCRIPTION OF THE INVENTION

I. Definitions

Figure 1:
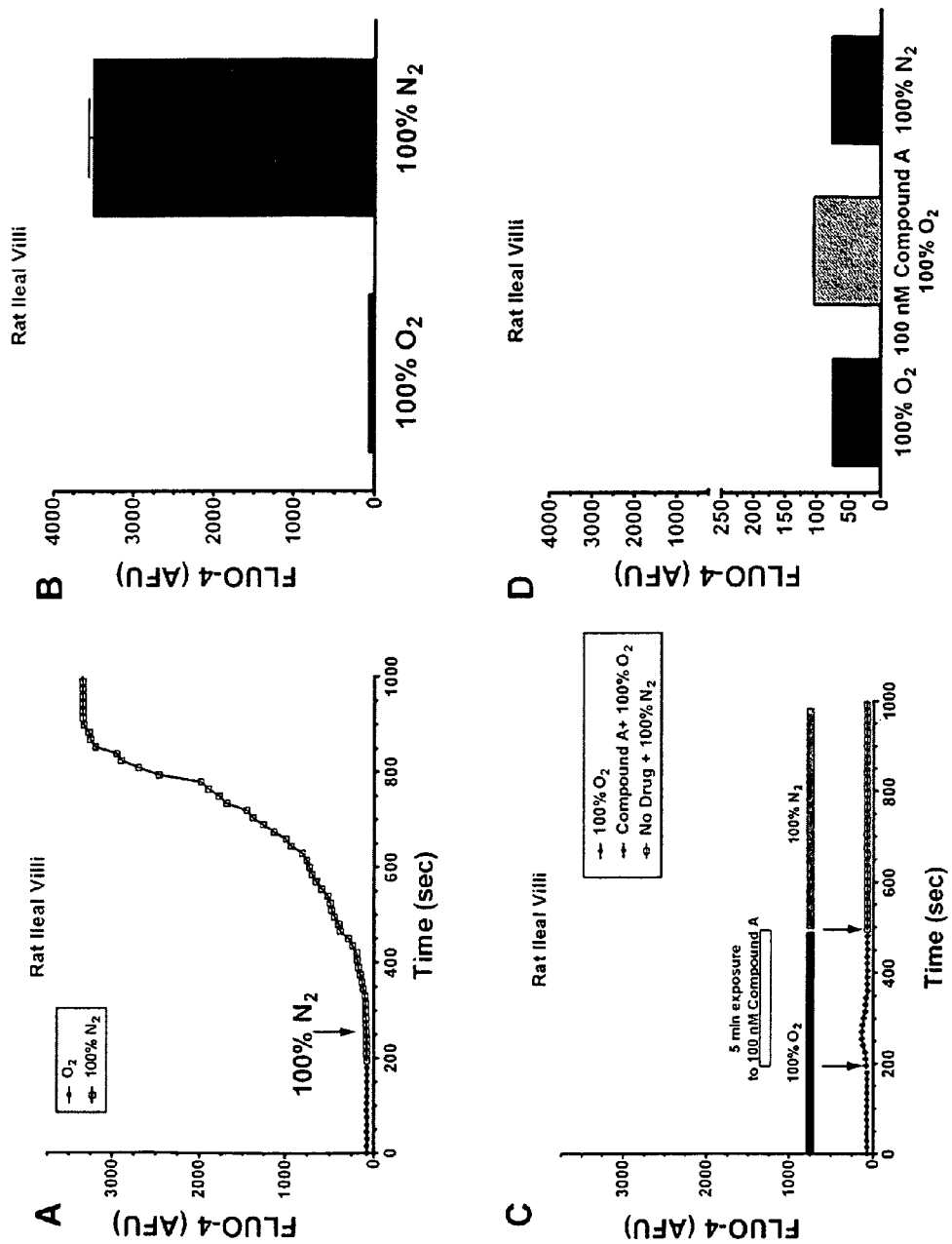
FIG. 1 illustrates the effect of a calcimimetic compound A on protection from ischemic injury in isolated ileal villi from a rat. Panel A shows a time course for changes in intracellular calcium following exposure to 100% $N_2$ (ischemic injury). Panel B is a summary of change in intracellular calcium in a ileal villus following $N_2$ exposure. Panel C illustrates the protective effect of a 5 min exposure to a calcimimetic (100 nM compound A) showing no increase in calcium in the presence of 100% $N_2$. Panel D is a summary of the protective effect of a calcimimetic (100 nM compound A) on villi exposed to ischemic injury.

As used herein, the term "subject" is intended to mean a human, or an animal, in need of a treatment. This subject can have, or be at risk of developing, epithelial injury due to, for example, ischemia, hypoxia, chemolytic agents or radiation exposure.

"Treating" or "treatment" of a disease includes: (1) inhibiting the disease, i.e., arresting or reducing the development of the disease or any of its clinical symptoms, or (2) preventing the disease, i.e., causing the clinical symptoms of the disease not to develop in a subject that may be or has been exposed to the disease or conditions that may cause the disease, or predisposed to the disease but does not yet experience or display symptoms of the disease, (3) relieving the disease, i.e., causing regression of the disease or any of its clinical symptoms.

Administration "in combination with" or "together with" one or more further therapeutic agents includes simultaneous or concurrent administration and consecutive administration in any order.

The phrase "therapeutically effective amount" is the amount of the compound of the invention that will achieve the goal of improvement in disorder severity and the frequency of incidence. The improvement in disorder severity includes the reversal of the disease, as well as slowing down the progression of the disease.

As used herein, "calcium sensing receptor" or "CaSR" refers to the G-protein-coupled receptor responding to changes in extracellular calcium and/or magnesium levels. Activation of the CaSR produces rapid, transient increases in cytosolic calcium concentration by mobilizing calcium from thapsigargin-sensitive intracellular stores and by increasing calcium influx though voltage-insensitive calcium channels in the cell membrane (Brown et al., Nature 366: 575-580, 1993; Yamaguchi et al., *Adv Pharmacol* 47: 209-253, 2000).

The term "epithelial injury" as used herein encompasses cellular injury due to ischemia, hypoxia, chemotherapy, radiation or trauma.

The term "radiation" encompasses both ionizing and non-ionizing types of radiation and includes infrared radiation, ultraviolet radiation, $\alpha$, $\beta$, $\gamma$, and X radiation.

"Ultraviolet" or UV light, as used herein, means electromagnetic energy having a wavelength between about 10 and 400 nm. The ultraviolet spectrum is arbitrarily divided into three major segments, UV-A light at wavelengths from about 320 to 400 nm, UV-B light at wavelength from 290 to 320 nm and UV-C light at wavelengths from about 10 to 290 nm. The UV-B portion of the UV spectrum is predominantly responsible for producing the redness or erythema of sunburn, whereas the UV-A light is approximately a thousand fold less efficient in producing skin hyperemia or sunburn. UV-C light from the sun is absorbed by stratospheric ozone.

"Chemolytics" or "chemolytic agents" as used herein, mean any agent that is used in chemotherapy. Examples of chemolytics include alkylating drugs (e.g., cyclophosphamide), this type of drugs alkylate DNA; antimetabolites (e.g., 5-fluorouracil (5-FU)) that interfere with the production of DNA and keep cells from growing and multiplying; antitumor antibiotics (e.g., doxorubicin and bleomycin) that are made from fungi; plant alkaloids (e.g., vinblastine and vincristine) that interfere with normal cell division; and steroid hormones (e.g., tamoxiphen), mainly used in hormone-depending cancers. Other examples of chemolytic agents or chemotherapy drugs are well known in the art.

II. Calcimimetics Compounds and Pharmaceutical Compositions Comprising them, Administration and Dosage

A. Calcimimetic Compounds, Definitions

As used herein, the term "calcimimetic compound" or "calcimimetic" refers to a compound that binds to calcium sensing receptors and induces a conformational change that reduces the threshold for calcium sensing receptor activation by the endogenous ligand $Ca^{2+}$. These calcimimetic compounds can also be considered allosteric modulators of the calcium receptors.

In one aspect, a calcimimetic can have one or more of the following activities: it evokes a transient increase in internal calcium, having a duration of less that 30 seconds (for example, by mobilizing internal calcium); it evokes a rapid increase in $[Ca^{2+}{}_i]$, occurring within thirty seconds; it evokes a sustained increase (greater than thirty seconds) in $[Ca^{2+}{}_i]$ (for example, by causing an influx of external calcium); evokes an increase in inositol-1,4,5-triphosphate or diacylglycerol levels, usually within less than 60 seconds; and inhibits dopamine- or isoproterenol-stimulated cyclic AMP formation. In one aspect, the transient increase in $[Ca^{2+}{}_i]$ can be abolished by pretreatment of the cell for ten minutes with 10 mM sodium fluoride or with an inhibitor of phospholipase C, or the transient increase is diminished by brief pretreatment (not more than ten minutes) of the cell with an activator of protein kinase C, for example, phorbol myristate acetate (PMA), mezerein or (−) indolactam V. In one aspect, a calcimimetic compound can be a small molecule. In another aspect, a calcimimetic can be an agonistic antibody to the CaSR.

Calcimimetic compounds useful in the present invention include those disclosed in, for example, European Patent Nos. 637,237, 657,029, 724,561, 787,122, 907,631, 933,354, 1,203,761, 1,235 797, 1,258,471, 1,275,635, 1,281,702, 1,284,963, 1,296,142, 1,308,436, 1,509,497, 1,509,518, 1,553,078; International Publication Nos. WO 93/04373, WO 94/18959, WO 95/11221, WO 96/12697, WO 97/41090, WO 01/34562, WO 01/90069, WO 02/14259, WO 02/059102, WO 03/099776, WO 03/099814, WO 04/017908; WO 04/094362, WO 04/106280, WO 06/117211; WO 06/123725; U.S. Pat. Nos. 5,688,938, 5,763,569, 5,962,314, 5,981,599, 6,001,884, 6,011,068, 6,031,003, 6,172,091, 6,211,244, 6,313,146, 6,342,532, 6,362,231, 6,432,656, 6,710,088, 6,750,255, 6,908,935, 7,157,498, 7,176,322 and U.S. Patent Application Publication No. 2002/0107406, 2003/0008876, 2003/0144526, 2003/0176485, 2003/0199497, 2004/0006130, 2004/0077619, 2005/0032796, 2005/0107448, 2005/0143426, European patent application PCT/EP2006/004166, French patent application 0511940.

In certain embodiments, the calcimimetic compound is chosen from compounds of Formula I and pharmaceutically acceptable salts thereof:

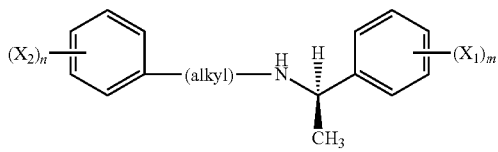

I wherein:

$X_1$ and $X_2$, which may be identical or different, are each a radical chosen from $CH_3$, $CH_3O$, $CH_3CH_2O$, Br, Cl, F, $CF_3$, $CHF_2$, $CH_2F$, $CF_3O$, $CH_3S$, OH, $CH_2OH$, $CONH_2$, CN, $NO_2$, $CH_3CH_2$, propyl, isopropyl, butyl, isobutyl, t-butyl, acetoxy, and acetyl radicals, or two of $X_1$ may together form an entity chosen from fused cycloaliphatic rings, fused aromatic rings, and a methylene dioxy radical, or two of $X_2$ may together form an entity chosen from fused cycloaliphatic rings, fused aromatic rings, and a methylene dioxy radical; provided that $X_2$ is not a 3-t-butyl radical;

n ranges from 0 to 5;

m ranges from 1 to 5; and the alkyl radical is chosen from C1-C3 alkyl radicals, which are optionally substituted with at least one group chosen from saturated and unsaturated, linear, branched, and cyclic C1-C9 alkyl groups, dihydroindolyl and thiodihydroindolyl groups, and 2-, 3-, and 4-piperid(in)yl groups.

The calcimimetic compound may also be chosen from compounds of Formula II:

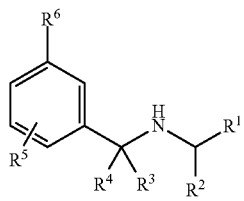

II and pharmaceutically acceptable salts thereof,
wherein:

$R^1$ is aryl, substituted aryl, heterocyclyl, substituted heterocyclyl, cycloalkyl, or substituted cycloalkyl;

$R^2$ is alkyl or haloalkyl;

$R^3$ is H, alkyl, or haloalkyl;

$R^4$ is H, alkyl, or haloalkyl;

each $R^5$ present is independently selected from the group consisting of alkyl, substituted alkyl, alkoxy, substituted alkoxy, halogen, —C(=O)OH, —CN, —$NR^dS(=O)_mR^d$, —$NR^dC(=O)NR^aR^d$, —$NR^aS(=O)_mNR^aR^d$, or —$NR^dC(=O)R^d$;

$R^6$ is aryl, substituted aryl, heterocyclyl, substituted heterocyclyl, cycloalkyl, or substituted cycloalkyl;

each $R^a$ is, independently, H, alkyl or haloalkyl;

each $R^b$ is, independently, aryl, aralkyl, heterocyclyl, or heterocyclylalkyl, each of which may be unsubstituted or substituted by up to 3 substituents selected from the group consisting of alkyl, halogen, haloalkyl, alkoxy, cyano, and nitro;

each $R^c$ is, independently, alkyl, haloalkyl, phenyl or benzyl, each of which may be substituted or unsubstituted;

each $R^d$ is, independently, H, alkyl, aryl, aralkyl, heterocyclyl, or heterocyclylalkyl wherein the alkyl, aryl, aralkyl, heterocyclyl, and heterocyclylalkyl are substituted by 0, 1, 2, 3 or 4 substituents selected from alkyl, halogen, haloalkyl, alkoxy, cyano, nitro, $R^b$, —C(=O)$R^c$, —$OR^b$, —$NR^aR^a$, —$NR^aR^b$, —C(=O)$OR^c$, —C(=O)$NR^aR^a$, —OC(=O)$R^c$, —$NR^aC(=O)R^c$, —$NR^aS(=O)_nR^c$ and —$S(=O)_nNR^aR^a$;

m is 1 or 2;

n is 0, 1 or 2; and p is 0, 1, 2, 3, or 4;

provided that if $R^2$ is methyl, p is 0, and $R^6$ is unsubstituted phenyl, then $R^1$ is not 2,4-dihalophenyl, 2,4-dimethylphenyl, 2,4-diethylphenyl, 2,4,6-trihalophenyl, or 2,3,4-trihalophenyl. These compounds are described in detail in published US patent application number 20040082625.

In one aspect, the calcimimetic compound can be N-((6-(methyloxy)-4'-(trifluoromethyl)-1,1'-biphenyl-3-yl)methyl)-1-phenylethanamine, or a pharmaceutically acceptable salt thereof. In another aspect, the calcimimetic compound can be (1R)—N-((6-chloro-3'-fluoro-3-biphenylyl)methyl)-1-(3-chlorophenyl)ethanamine, or a pharmaceutically acceptable salt thereof. In a further aspect, the calcimimetic compound can be (1R)-1-(6-(methyloxy)-4'-(trifluoromethyl)-3-biphenylyl)-N-((1R)-1-phenylethyl)ethanamine, or a pharmaceutically acceptable salt thereof.

In certain embodiments of the invention the calcimimetic compound can be chosen from compounds of Formula III

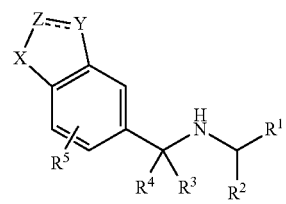

III and pharmaceutically acceptable salts thereof, wherein:
----- represents a double or single bond;
$R^1$ is $R^b$;
$R^2$ is $C_{1-8}$ alkyl or $C_{1-4}$ haloalkyl;
$R^3$ is H, $C_{1-4}$ haloalkyl or $C_{1-8}$ alkyl;
$R^4$ is H, $C_{1-4}$ haloalkyl or $C_{1-4}$ alkyl;
$R^5$ is, independently, in each instance, H, $C_{1-8}$ alkyl, $C_{1-4}$ haloalkyl, halogen, —$OC_{1-6}$ alkyl, —$NR^aR^d$ or $NR^dC(=O)R^d$;
X is —$CR^d=N$—, —$N=CR^d$—, O, S or —$NR^d$—;
when ----- is a double bond then Y is =$CR^6$— or =N— and Z is —$CR^7$= or —N=; and when ----- is a single bond then Y is —$CR^aR^6$— or —$NR^d$— and Z is —$CR^aR^7$— or —$NR^d$—; and
$R^6$ is $R^d$, $C_{1-4}$ haloalkyl, —C(=O)$R^c$, —$OC_{1-6}$ alkyl, —$OR^b$, —$NR^aR^a$, —$NR^aR^b$, —C(=O)$OR^c$, —C(=O)$NR^aR^a$, —OC(=O)$R^c$, —$NR^aC(=O)R^c$, cyano, nitro, —$NR^aS(=O)_mR^c$ or —$S(=O)_mNR^aR^a$;

$R^7$ is $R^d$, $C_{1-4}$haloalkyl, —C(═O)$R^c$, —O$C_{1-6}$alkyl, —O$R^b$, —N$R^aR^a$, —N$R^aR^b$, —C(═O)O$R^c$, —C(═O)N$R^aR^a$, —OC(═O)$R^c$, —N$R^a$C(═O)$R^c$, cyano, nitro, —N$R^a$S(═O)$_mR^c$ or —S(═O)$_m$N$R^aR^a$; or $R^6$ and $R^7$ together form a 3- to 6-atom saturated or unsaturated bridge containing 0, 1, 2 or 3 N atoms and 0, 1 or 2 atoms selected from S and O, wherein the bridge is substituted by 0, 1 or 2 substituents selected from $R^5$; wherein when $R^6$ and $R^7$ form a benzo bridge, then the benzo bridge may be additionally substituted by a 3- or 4-atoms bridge containing 1 or 2 atoms selected from N and O, wherein the bridge is substituted by 0 or 1 substituents selected from $C_{1-4}$alkyl;

$R^a$ is, independently, at each instance, H, $C_{1-4}$haloalkyl or $C_{1-6}$alkyl;

$R^b$ is, independently, at each instance, phenyl, benzyl, naphthyl or a saturated or unsaturated 5- or 6-membered ring heterocycle containing 1, 2 or 3 atoms selected from N, O and S, with no more than 2 of the atoms selected from O and S, wherein the phenyl, benzyl or heterocycle are substituted by 0, 1, 2 or 3 substituents selected from $C_{1-6}$alkyl, halogen, $C_{1-4}$haloalkyl, —O$C_{1-6}$alkyl, cyano and nitro;

$R^c$ is, independently, at each instance, $C_{1-6}$alkyl, $C_{1-4}$haloalkyl, phenyl or benzyl;

$R^d$ is, independently, at each instance, H, $C_{1-6}$alkyl, phenyl, benzyl or a saturated or unsaturated 5- or 6-membered ring heterocycle containing 1, 2 or 3 atoms selected from N, O and S, with no more than 2 of the atoms selected from O and S, wherein the $C_{1-6}$alkyl, phenyl, benzyl, naphthyl and heterocycle are substituted by 0, 1, 2, 3 or 4 substituents selected from $C_{1-6}$alkyl, halogen, $C_{1-4}$haloalkyl, —O$C_{1-6}$alkyl, cyano and nitro, $R^b$, —C(═O)$R^c$, —O$R^b$, —N$R^aR^a$, —N$R^aR^b$, —C(═O)O$R^c$, —C(═O)N$R^aR^a$, —OC(═O)$R^c$, —N$R^a$C(═O)$R^c$, —N$R^a$S(═O)$_mR^c$ and —S(═O)$_m$N$R^aR^a$; and m is 1 or 2.

Compounds of Formula III are described in detail in U.S. patent application 20040077619, which is incorporated herein by reference.

In one aspect, a calcimimetic compound is N-(3-[2-chlorophenyl]-propyl)-R-■-methyl-3-methoxybenzylamine HCl (Compound A). In another aspect, a calcimimetic compound is N-((6-(methyloxy)-4'-(trifluoromethyl)-1,1'-biphenyl-3-yl)methyl)-1-phenylethanamine (Compound B).

In one aspect, the calcimimetic compound of the invention can be chose from compounds of Formula IV

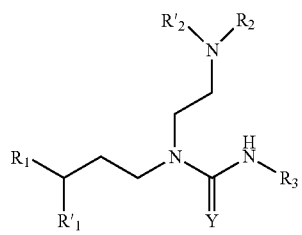

IV wherein:

Y is oxygen or sulphur;

$R_1$ and $R'_1$ are the same or different, and each represents an aryl group, a heteroaryl group, or $R_1$ and $R'_1$, together with the carbon atom to which they are linked, form a fused ring structure of formula:

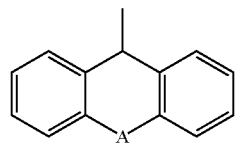

in which A represents a single bond, a methylene group, a dimethylene group, oxygen, nitrogen or sulphur, said sulphur optionally being in the sulphoxide or sulphone forms, wherein each of $R_1$ and $R'_1$, or said fused ring structure formed thereby, is optionally substituted by at least one substituent selected from the group c, wherein the group c consists of: halogen atoms, hydroxyl, carboxyl, linear and branched alkyl, hydroxyalkyl, haloalkyl, alkylthio, alkenyl, and alkynyl groups; linear and branched alkoxyl groups; linear and branched thioalkyl groups; hydroxycarbonylalkyl; alkylcarbonyl; alkoxycarbonylalkyl; alkoxycarbonyl; trifluoromethyl; trifluoromethoxy; —CN; —NO$_2$; alkylsulphonyl groups optionally in the sulphoxide or sulphone forms; wherein any alkyl component has from 1 to 6 carbon atoms, and any alkenyl or alkynyl components have from 2 to 6 carbon atoms, and wherein, when there is more than one substituent, then each said substituent is the same or different, $R_2$ and $R'_2$, which may be the same or different, each represents: a hydrogen atom; a linear or branched alkyl group containing from 1 to 6 carbon atoms and optionally substituted by at least one halogen atom, hydroxy or alkoxy group containing from 1 to 6 carbon atoms; an alkylaminoalkyl or dialkylaminoalkyl group wherein each alkyl group contains from 1 to 6 carbon atoms, or $R_2$ and $R'_2$, together with the nitrogen atom to which they are linked, form a saturated or unsaturated heterocycle containing 0, 1 or 2 additional heteroatoms and having 5, 6, or 7 ring atoms, said heterocycle being optionally substituted by at least one substituent selected from the group 'c' defined above, and wherein, when there is more than one substituent, said substituent is the same or different, $R_3$ represents a group of formula:

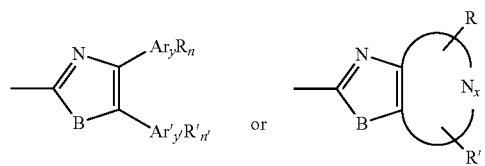

in which B represents an oxygen atom or a sulphur atom, x is 0, 1 or 2, y and y' are the same or different, and each is 0 or 1, Ar and Ar' are the same or different and each represents an aryl or heteroaryl group, n and n' are the same or different, and each is 1, when the y or y' with which it is associated is 0, or is equal to the number of positions that can be substituted on the associated Ar or Ar' when the said y or y' is 1, the fused ring containing $N_x$ is a five- or six-membered heteroaryl ring, and wherein R and R', which may be the same or different, each represent a hydrogen atom or a substituent selected from the group a, wherein the group a consists of: halogen atoms; hydroxyl; carboxyl; aldehyde groups; linear and branched alkyl, alkenyl, alkynyl, hydroxyalkyl, hydroxyalkenyl, hydroxyalkynyl, haloalkyl, haloalkenyl, and haloalkynyl groups; linear and branched alkoxyl groups; linear and branched thioalkyl groups; aralkoxy groups; aryloxy groups; alkoxycarbonyl; aralkoxycarbonyl; aryloxycarbonyl; hydroxycarbonylalkyl; alkoxycarbonylalkyl; aralkoxycarbonylalkyl; aryloxycarbonylalkyl; perfluoroalkyl; perfluoroalkoxy; —CN; acyl; amino, alkylamino, aralkylamino, arylamino, dialkylamino, diaralkylamino, diarylamino, acylamino, and diacylamino groups; alkoxycarbonylamino, aralkoxycarbonylamino, aryloxycarbonylamino, alkylcarbonylamino, aralkylcarbonylamino, and arylcarbonylamino groups; alkylaminocarbonyloxy, aralkylaminocarbonyloxy, and arylaminocarbonyloxy groups; alkyl groups substituted with an amino, alkylamino, aralkylamino, arylamino, dialkylamino, diaralkylamino, diarylamino, acylamino, trifluoromethylcarbonyl-amino, fluoroalkylcarbonylamino, or diacylamino group; $CONH_2$; alkyl-, aralkyl-, and aryl-amido groups; alkylthio, arylthio and aralkylthio and the oxidised sulphoxide and sulphone forms thereof; sulphonyl, alkylsulphonyl, haloalkylsulphonyl, arylsulphonyl and aralkylsulphonyl groups; sulphonamide, alkylsulphonamide, haloalkylsulphonamide, di(alkylsulphonyl)amino, aralkylsulphonamide, di(aralkylsulphonyl)amino, arylsulphonamide, and di(arylsulphonyl)amino; and saturated and unsaturated heterocyclyl groups, said heterocyclyl groups being mono- or bi-cyclic and being optionally substituted by one or more substituents, which may be the same or different, selected from the group b, wherein the group b consists of: halogen atoms; hydroxyl; carboxyl; aldehyde groups; linear and branched alkyl, alkenyl, alkynyl, hydroxyalkyl, hydroxyalkenyl, hydroxyalkynyl, haloalkyl, haloalkenyl, and haloalkynyl groups; linear and branched alkoxyl groups; linear and branched thioalkyl groups; alkoxycarbonyl; hydroxycarbonylalkyl; alkoxycarbonylalkyl; perfluoroalkyl; perfluoroalkoxy; —CN; acyl; amino, alkylamino, dialkylamino, acylamino, and diacylamino groups; alkyl groups substituted with an amino, alkylamino, dialkylamino, acylamino, or diacylamino group; $CONH_2$; alkylamido groups; alkylthio and the oxidised sulphoxide and sulphone forms thereof; sulphonyl, alkylsulphonyl groups; and sulphonamide, alkylsulphonamide, and di(alkylsulphonyl)amino groups, wherein, in groups a and b, any alkyl components contain from 1 to 6 carbon atoms, and any alkenyl or alkynyl components contain from 2 to 6 carbon atoms, and are optionally substituted by at least one halogen atom or hydroxy group, and wherein any aryl component is optionally a heteroaryl group.

In one aspect, the calcimimetic compound can be 3-(1,3-benzothiazol-2-yl)-1-(3,3-diphenylpropyl)-1-(2-(4-morpholinyl)ethyl)urea or pharmaceutically acceptable salt thereof. In another aspect, the calcimimetic compound can be N-(4-(2-((((3,3-diphenylpropyl)(2-(4-morpholinyl)ethyl)amino)carbonyl)amino)-1,3-thiazol-4-yl)phenyl)methanesulfonamide or pharmaceutically acceptable salt thereof.

In one aspect, the calcimimetic compound of the invention can be chose from compounds of Formula V

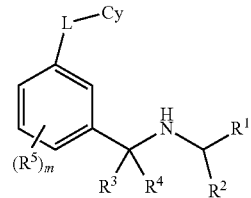

wherein:

$R^1$ is phenyl, benzyl, naphthyl or a saturated or unsaturated 5- or 6-membered heterocyclic ring containing 1, 2 or 3 atoms selected from N, O and S, with no more than 2 of the atoms selected from O and S, wherein the phenyl, benzyl, naphthyl or heterocyclic ring are substituted by 0, 1, 2 or 3 substituents selected from $C_{1-6}$alkyl, halogen, $C_{1-4}$haloalkyl, —$OC_{1-6}$alkyl, cyano and nitro;

$R^2$ is $C_{1-8}$alkyl or $C_{1-4}$haloalkyl;

$R^3$ is H, $C_{1-4}$haloalkyl or $C_{1-8}$alkyl;

$R^4$ is H, $C_{1-4}$haloalkyl or $C_{1-8}$alkyl;

$R^5$ is, independently, in each instance, H, $C_{1-8}$alkyl, $C_{1-4}$haloalkyl, halogen, —$OC_{1-6}$alkyl, —$NR^aR^d$, $NR^aC(=O)R^d$, substituted or unsubstituted pyrrolidinyl, substituted or unsubstituted azetidinyl, or substituted or unsubstituted piperidyl, wherein the substituents can be selected from halogen, —$OR^b$, —$NR^aR^d$, —$C(=O)OR^c$, —$C(=O)NR^aR^d$, —$OC(=O)R^c$, —$NR^aC(=O)R^c$, cyano, nitro, —$NR^aS(=O)_nR^c$ or —$S(=O)_nNR^aR^d$;

L is —O—, —$OC_{1-6}$alkyl-, —$C_{1-6}$alkylO-, —$N(R^a)(R^d)$—, —$NR^aC(=O)$—, —$C(=O)$—, —$C(=O)NR^dC_{1-6}$alkyl-, —$C_{1-6}$alkyl-$C(=O)NR^d$—, —$NR^dC(=O)NR^d$—, —$NR^dC(=O)NR^dC_{1-6}$alkyl-, —$NR^aC(=O)R^c$—, —$NR^aC(=O)OR^c$—, —$OC_{1-6}$alkyl-$C(=O)O$—, —$NR^dC_{1-6}$alkyl-, —$C_{1-6}$alkylNR^d$—, —S—, —$S(=O)_n$—, —$NR^aS(=O)_n$, or —$S(=O)_nN(R^a)$—;

Cy is a partially or fully saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, and wherein each ring of the ring system is optionally substituted independently with one or more substituents of $R^6$, $C_{1-8}$alkyl, $C_{1-4}$haloalkyl, halogen, cyano, nitro, —$OC_{1-6}$alkyl, —$NR^aR^d$, $NR^dC(=O)R^d$, —$C(=O)OR^c$, —$C(=O)NR^aR^d$, —$OC(=O)R^c$, —$NR^aC(=O)R^c$, —$NR^aS(=O)_mR^c$ or —$S(=O)_mNR^aR^d$;

$R^6$ is a partially or fully saturated or unsaturated 5-8 membered monocyclic, 6-12 membered bicyclic, or 7-14 membered tricyclic ring system, the ring system formed of carbon atoms optionally including 1-3 heteroatoms if monocyclic, 1-6 heteroatoms if bicyclic, or 1-9 heteroatoms if tricyclic, and wherein each ring of the ring system is optionally substituted independently with one or more substituents of $C_{1-8}$alkyl, $C_{1-4}$haloalkyl, halogen, cyano, nitro, —$OC_{1-6}$alkyl, —$NR^aR^d$, $NR^dC(=O)R^d$, —$C(=O)OR^c$, —$C(=O)NR^aR^d$, —$OC(=O)R^c$, —$NR^aC(=O)R^c$, —$NR^aS(=O)_mR^c$ or —$S(=O)_mNR^aR^d$;

$R^a$ is, independently, at each instance, H, $C_{1-4}$haloalkyl, $C_{1-6}$alkyl, $C_{1-6}$alkenyl, $C_{1-6}$alkylaryl or aryl$C_{1-6}$alkyl:

$R^b$ is, independently, at each instance, $C_{1-8}$alkyl, $C_{1-4}$haloalkyl, phenyl, benzyl, naphthyl or a saturated or unsaturated 5- or 6-membered heterocyclic ring containing 1, 2 or 3 atoms selected from N, O and S, with no more than 2 of the atoms selected from O and S, wherein the phenyl, benzyl, naphthyl or heterocyclic ring are substituted by 0, 1, 2 or 3 substituents selected from $C_{1-6}$alkyl, halogen, $C_{1-4}$haloalkyl, —$OC_{1-6}$alkyl, cyano and nitro;

$R^c$ is, independently, at each instance, $C_{1-6}$alkyl, $C_{1-4}$haloalkyl, phenyl or benzyl;

$R^d$ is, independently, at each instance, H, $C_{1-6}$alkyl, $C_{1-6}$alkenyl, phenyl, benzyl, naphthyl or a saturated or unsaturated 5- or 6-membered heterocycle ring containing 1, 2 or 3 atoms selected from N, O and S, with no more than 2 of the atoms selected from O and S, wherein the $C_{1-6}$alkyl, phenyl, benzyl, naphthyl and heterocycle are substituted by 0, 1, 2, 3 or 4 substituents selected from $C_{1-6}$alkyl, halogen, $C_{1-4}$haloalkyl, —$OC_{1-6}$alkyl, cyano and nitro, $R^b$, —C(=O)$R^c$, —O$R^b$, —N$R^a R^b$, —C(=O)O$R^c$, —C(=O)N$R^a R^b$, —OC(=O)$R^c$, —N$R^a$C(=O)$R^c$, —N$R^a$S(=O)$_m R^c$ and —S(=O)$_m$ N$R^a R^a$;

m is 1 or 2;

n is 1 or 2;

provided that if L is —O— or —$OC_{1-6}$alkyl-, then Cy is not phenyl.

In one aspect, the calcimimetic compound can be N-(2-chloro-5-(((((1R)-1-phenylethyl)amino)methyl)phenyl)-5-methyl-3-isoxazolecarboxamide or a pharmaceutically acceptable salt thereof. In another aspect, the calcimimetic compound can be N-(2-chloro-5-((((1R)-1-phenylethyl)amino)methyl)phenyl)-2-pyridinecarboxamide or a pharmaceutically acceptable salt thereof.

Calcimimetic compounds useful in the methods of the invention include the calcimimetic compounds described above, as well as their stereoisomers, enantiomers, polymorphs, hydrates, and pharmaceutically acceptable salts of any of the foregoing.

B. Methods of Assessing Calcimimetic Activity

In one aspect, compounds binding at the CaSR-activity modulating site can be identified using, for example, a labeled compound binding to the site in a competition-binding assay format.

Calcimimetic activity of a compound can be determined using techniques such as those described in International Publications WO 93/04373, WO 94/18959 and WO 95/11211.

Other methods that can be used to assess compounds calcimimetic activity are described below.

HEK 293 Cell Assay

HEK 293 cells engineered to express human parathyroid CaSR (HEK 293 4.0-7) have been described in detail previously (Nemeth E F et al. (1998) Proc. Natl. Acad. Sci. USA 95:4040-4045). This clonal cell line has been used extensively to screen for agonists, allosteric modulators, and antagonists of the CaSR (Nemeth E F et al. (2001) J. Pharmacol. Exp. Ther. 299:323-331).

For measurements of cytoplasmic calcium concentration, the cells are recovered from tissue culture flasks by brief treatment with 0.02% ethylenediaminetetraacetic acid (EDTA) in phosphate-buffered saline (PBS) and then washed and resuspended in Buffer A (126 mM NaCl, 4 mM KCl, 1 mM CaCl$_2$, 1 mM MgSO$_4$, 0.7 mM K$_2$HPO$_4$/KH$_2$PO$_4$, 20 mM Na-Hepes, pH 7.4) supplemented with 0.1% bovine serum albumin (BSA) and 1 mg/ml D-glucose. The cells are loaded with fura-2 by incubation for 30 minutes at 37° C. in Buffer A and 2 µM fura-2 acetoxymethylester. The cells are washed with Buffer B (Buffer B is Buffer A lacking sulfate and phosphate and containing 5 mM KCl, 1 mM MgCl$_2$, 0.5 mM CaCl$_2$ supplemented with 0.5% BSA and 1 mg/ml D-glucose) and resuspended to a density of 4 to 5×10$^6$ cells/ml at room temperature. For recording fluorescent signals, the cells are diluted five-fold into prewarmed (37° C.) Buffer B with constant stirring. Excitation and emission wavelengths are 340 and 510 nm, respectively. The fluorescent signal is recorded in real time using a strip-chart recorder.

For fluorometric imaging plate reader (FLIPR) analysis, HEK 293 cells are maintained in Dulbecco's modified Eagle's medium (DMEM) with 10% fetal bovine serum (FBS) and 200 µg/ml hygromycin. At 24 hrs prior to analysis, the cells are trypsinized and plated in the above medium at 1.2×10$^5$ cells/well in black sided, clear-bottom, collagen 1-coated, 96-well plates. The plates are centrifuged at 1,000 rpm for 2 minutes and incubated under 5% CO$_2$ at 37° C. overnight. Cells are then loaded with 6 µM fluo-3 acetoxymethylester for 60 minutes at room temperature. All assays are performed in a buffer containing 126 mM NaCl, 5 mM KCl, 1 mM MgCl$_2$, 20 mM Na-Hepes, supplemented with 1.0 mg/ml D-glucose and 1.0 mg/ml BSA fraction IV (pH 7.4).

In one aspect, the EC$_{50}$'s for the CaSR-active compounds can be determined in the presence of 1 mM Ca$^{2+}$. The EC$_{50}$ for cytoplasmic calcium concentration can be determined starting at an extracellular Ca$^{2+}$ level of 0.5 mM. FLIPR experiments are done using a laser setting of 0.8 W and a 0.4 second CCD camera shutter speed. Cells are challenged with calcium, CaSR-active compound or vehicle (20 µl) and fluorescence monitored at 1 second intervals for 50 seconds. Then a second challenge (50 µl) of calcium, CaSR-active compound, or vehicle can be made and the fluorescent signal monitored. Fluorescent signals are measured as the peak height of the response within the sample period. Each response is then normalized to the maximum peak observed in the plate to determine a percentage maximum fluorescence.

Bovine Parathyroid Cells

The effect of calcimimetic compounds on CaSR-dependent regulation of PTH secretion can be assessed using primary cultures of dissociated bovine parathyroid cells. Dissociated cells can be obtained by collagenase digestion, pooled, then resuspended in Percoll purification buffer and purified by centrifugation at 14,500×g for 20 minutes at 4° C. The dissociated parathyroid cells are removed and washed in a 1:1 mixture of Ham's F-12 and DMEM (F-12/DMEM) supplemented with 0.5% BSA, 100 U/ml penicillin, 100 µg/ml streptomycin, and 20 µg/ml gentamicin. The cells are finally resuspended in F-12/DMEM containing 10 U/ml penicillin, 10 µg/ml streptomycin, and 4 µg/ml gentamicin, and BSA was substituted with ITS+ (insulin, transferrin, selenous acid, BSA, and linoleic acid; Collaborative Research, Bedford, Mass.). Cells are incubated in T-75 flasks at 37° C. in a humidified atmosphere of 5% CO$_2$ in air.

Following overnight culture, the cells are removed from flasks by decanting and washed with parathyroid cell buffer (126 mM NaCl, 4 mM KCl, 1 mM MgSO$_4$, 0.7 mM K$_2$HPO$_4$/KH$_2$PO$_4$, 20 mM Na-Hepes, 20; pH 7.45 and variable amounts of CaCl$_2$ as specified) containing 0.1% BSA and 0.5 mM CaCl$_2$. The cells are resuspended in this same buffer and portions (0.3 ml) are added to polystyrene tubes containing appropriate controls, CaSR-active compound, and/or varying concentrations of CaCl$_2$. Each experimental condition is performed in triplicate. Incubations at 37° C. are for 20 minutes and can be terminated by placing the tubes on ice. Cells are pelleted by centrifugation (1500×g for 5 minutes at 4° C.) and 0.1 ml of supernatant is assayed immediately. A portion of the cells is left on ice during the incubation period and then processed in parallel with other samples. The amount of PTH in the supernatant from tubes maintained on ice is defined as "basal release" and subtracted from other samples. PTH is measured according to the vendor's instructions using rat PTH-(1-34) immunoradiometric assay kit (Immunotopics, San Clemente, Calif.).

MTC 6-23 Cell Calcitonin Release

Rat MTC 6-23 cells (clone 6), purchased from ATCC (Manassas, Va.) are maintained in growth media (DMEM high glucose with calcium/15% HIHS) that is replaced every 3 to 4 days. The cultures are passaged weekly at a 1:4 split ratio. Calcium concentration in the formulated growth media is calculated to be 3.2 mM. Cells are incubated in an atmosphere of 90% $O_2$/10% $CO_2$, at 37° C. Prior to the experiment, cells from sub-confluent cultures are aspirated and rinsed once with trypsin solution. The flasks are aspirated again and incubated at room temperature with fresh trypsin solution for 5-10 minutes to detach the cells. The detached cells are suspended at a density of $3.0 \times 10^5$ cells/mL in growth media and seeded at a density of $1.5 \times 10^5$ cells/well (0.5 mL cell suspension) in collagen-coated 48 well plates (Becton Dickinson Labware, Bedford, Mass.). The cells are allowed to adhere for 56 hours post-seeding, after which the growth media was aspirated and replaced with 0.5 mL of assay media (DMEM high glucose without/2% FBS). The cells are then incubated for 16 hours prior to determination of calcium-stimulated calcitonin release. The actual calcium concentration in this media is calculated to be less than 0.07 mM. To measure calcitonin release, 0.35 mL of test agent in assay media is added to each well and incubated for 4 hours prior to determination of calcitonin content in the media. Calcitonin levels are quantified according to the vendor's instructions using a rat calcitonin immunoradiometric assay kit (Immutopics, San Clemente, Calif.).

Inositol Phosphate Assay

The calcimimetic properties of compounds could also be evaluated in a biochemical assay performed on Chinese hamster ovarian (CHO) cells transfected with an expression vector containing cloned CaSR from rat brain [CHO(CaSR)] or not [CHO(WT)] (Ruat M., Snowman A M., J. Biol. Chem. 271, 1996, p 5972). CHO(CaSR) has been shown to stimulate tritiated inositol phosphate ([$^3$H]IP) accumulation upon activation of the CaSR by $Ca^{2+}$ and other divalent cations and by NPS 568 (Ruat et al., J. Biol. Chem. 271, 1996). Thus, [$^{3H}$]IP accumulation produced by 10 μM of each CaSR-active compound in the presence of 2 mM extracellular calcium can be measured and compared to the effect produced by 10 mM extracellular calcium, a concentration eliciting maximal CaSR activation (Dauban P. et al., Bioorganic & Medicinal Chemistry Letters, 10, 2000, p 2001).

C. Pharmaceutical Compositions and Administration

Calcimimetic compounds useful in the present invention can be used in the form of pharmaceutically acceptable salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, mandelate, methansulfonate, nicotinate, 2-naphthalenesulfonate, oxalate, palmoate, pectinate, persulfate, 2-phenyl-propionate, picrate, pivalate, propionate, salicylate, succinate, sulfate, tartrate, thiocyanate, tosylate, mesylate, and undecanoate. When compounds of the invention include an acidic function such as a carboxy group, then suitable pharmaceutically acceptable salts for the carboxy group are well known to those skilled in the art and include, for example, alkaline, alkaline earth, ammonium, quaternary ammonium cations and the like. For additional examples of "pharmacologically acceptable salts," see Berge et al. *J. Pharm. Sci.* 66: 1, 1977. In certain embodiments of the invention salts of hydrochloride and salts of methanesulfonic acid can be used.

In some aspects of the present invention, the calcium-receptor active compound can be chosen from cinacalcet, i.e., N-(1-(R)-(1-naphthyl)ethyl]-3-[3-(trifluoromethyl)phenyl]-1-aminopropane, cinacalcet HCl, and cinacalcet methanesulfonate. The calcimimetic compound, such as cinacalcet HCl and cinacalcet methanesulfonate, can be in various forms such as amorphous powders, crystalline powders, and mixtures thereof. The crystalline powders can be in forms including polymorphs, psuedopolymorphs, crystal habits, micromeretics, and particle morphology.

For administration, the compounds useful in this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, the compounds useful in this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, suppositories, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

The therapeutically effective amount of the calcium receptor-active compound in the compositions useful in the invention can range from about 0.1 mg to about 180 mg, for example from about 5 mg to about 180 mg, or from about 1 mg to about 100 mg of the calcimimetic compound per subject. In some aspects, the therapeutically effective amount of calcium receptor-active compound in the composition can be chosen from about 0.1 mg, about 1 mg, 5 mg, about 15 mg, about 20 mg, about 30 mg, about 50 mg, about 60 mg, about 75 mg, about 90 mg, about 120 mg, about 150 mg, about 180 mg.

While it may be possible to administer a calcium receptor-active compound to a subject alone, the compound administered will normally be present as an active ingredient in a pharmaceutical composition. Thus, a pharmaceutical composition of the invention may comprise a therapeutically effective amount of at least one calcimimetic compound, or an effective dosage amount of at least one calcimimetic compound.

As used herein, an "effective dosage amount" is an amount that provides a therapeutically effective amount of the calcium receptor-active compound when provided as a single dose, in multiple doses, or as a partial dose. Thus, an effective dosage amount of the calcium receptor-active compound of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multidose pharmaceutical composition, such as powders, liquids and the like, in which an effective amount of the calcimimetic compound is administered by administering a portion of the composition.

Alternatively, a pharmaceutical composition in which two or more unit dosages, such as in tablets, capsules and the like, are required to administer an effective amount of the calcium receptor-active compound may be administered in less than an effective amount for one or more periods of time (e.g., a once-a-day administration, and a twice-a-day administration), for example to ascertain the effective dose for an individual subject, to desensitize an individual subject to potential side effects, to permit effective dosing readjustment or depletion of one or more other therapeutics administered to an individual subject, and/or the like.

The effective dosage amount of the pharmaceutical composition useful in the invention can range from about 1 mg to about 360 mg from a unit dosage form, for example about 5 mg, about 15 mg, about 30 mg, about 50 mg, about 60 mg, about 75 mg, about 90 mg, about 120 mg, about 150 mg, about 180 mg, about 210 mg, about 240 mg, about 300 mg, or about 360 mg from a unit dosage form.

In some aspects of the present invention, the compositions disclosed herein comprise a therapeutically effective amount of a calcium receptor-active compound for the treatment or prevention of epithelial injury. For example, in certain embodiments, the calcimimetic compound such as cinacalcet HCl can be present in an amount ranging from about 1% to about 70%, such as from about 5% to about 40%, from about 10% to about 30%, or from about 15% to about 20%, by weight relative to the total weight of the composition.

The compositions useful in the invention may contain one or more active ingredients in addition to the calcium sensing receptor-active compound. The additional active ingredient may be another calcimimetic compound, or it may be an active ingredient having a different therapeutic activity. When administered as a combination, the therapeutic agents can be formulated as separate compositions that are given at the same time or different times, or the therapeutic agents can be given as a single composition.

In one aspect, the pharmaceutical compositions useful for methods of the invention may include additional compounds as described in more detail below.

In another aspect, the compounds used to practice the methods of the instant invention can be formulated for oral administration that release biologically active ingredients in the colon without substantial release into the upper gastrointestinal tract, e.g. stomach and intestine. Oral delivery of drugs to the colon can allow achieving high local concentration while minimizing side effects that occur because of release of drugs in the upper GI tract or unnecessary systemic absorption. The advantage of colonic delivery of drugs can be due to the fact that poorly absorbed drugs may have an improved bioavailability, colon is somewhat less hostile environments with less diversity and intensity of activity that the stomach and small intestine, and the colon has a longer retention time and appears highly responsive to agents that enhance the absorption of poorly absorbed drugs. Chourasia, M. et al. (2003) *J. Pharm. Pharmaceut. Sci* 6(1): 33-66. Some pharmaceutical approaches that can be used for the development if colon targeted drug delivery systems are summarized in Table 1.

TABLE 1

| Approach | Basic Features |
| --- | --- |
| Covalent linkage of a drug and a carrier | |
| Azo conjugates | The drug is conjugated with an azo bond |
| Cyclodextrin conjugates | The drug is conjugated with cyclodextrin |
| Glycoside conjugates | The drug is conjugated with glycisode |
| Glucoronate conjugates | The drug is conjugated with glucoronate |
| Dextran conjugates | The drug is conjugated with dextran |
| Polypetide conjugates | The drug is conjugated with poly(aspartic acid) |
| Approaches to deliver the intact molecule to the colon | |
| Coating with pH-sensitive polymers | Formulation coated with enteric polymers releases drug when pH moves towards alkaline range |
| Coating with biodegradable polymers | Drug is released following degradation of the polymer due to the action of colonic bacteria |
| Embedding in biodegradable matrices and hydrogels | The embedded drug in polysaccharide matrices is released by swelling and by the biodegradable action of polysaccharidases |
| Embedding in pH-sensitive matrices | Degradation of the pH-sensitive polymer in the GI tract releases the embedded drug |
| Time released systems | Once the multicoated formulation passes the stomach, the drug is released after a lag time of 3-5 h that is equivalent to small intestine transit time |
| Redox-sensitive polymers | Drug formulated with azo polymer and disulfide polymers that selectively respond to the redox potential of the colon provides colonic delivery |
| Bioadhesive systems | Drug coated with a bioadhesive polymer that selectively provides adhesion to the colonic mucosa may release drug in the colon |
| Coating with microparticles | Drug is linked with microparticles |
| Osmotic controlled drug delivery | Drug is released through semipermeable membrane due to osmotic pressure |

In another example, pharmaceutical compositions of the invention can be used with the drug carrier including pectin and galactomannan, polysaccharides that are both degradable by colonic bacterial enzymes (U.S. Pat. No. 6,413,494). While pectin or galactomannan, if used alone as a drug carrier, are easily dissolved in simulated gastric fluid and simulated intestinal fluid, a mixture of these two polysaccharides prepared at a pH of about 7 or above produces a strong, elastic, and insoluble gel that is not dissolved or disintegrated in the simulated gastric and intestinal fluids, thus protecting drugs coated with the mixture from being released in the upper GI tract. When the mixture of pectin and galactomannan arrives in the colon, it is rapidly degraded by the synergic action of colonic bacterial enzymes. In yet another aspect, the compositions of the invention may be used with the pharmaceutical matrix of a complex of gelatin and an anionic polysaccharide (e.g., pectinate, pectate, alginate, chondroitin sulfate, polygalacturonic acid, tragacanth gum, arabic gum, and a mixture thereof), which is degradable by colonic enzymes (U.S. Pat. No. 6,319,518).

In another route of delivery of compounds of the invention, transdermal administration can be used to achieve therapeutic levels of the compounds in the systemic circulatory system, as well as for more localized internal dosing of drugs. It is often necessary to provide a composition containing a skin penetration enhancing vehicle in order to provide sufficient transdermal penetration of the drug to achieve therapeutic levels of the compounds at the target internal tissue. A number of skin penetration enhancing vehicles have been disclosed, including U.S. Pat. Nos. 4,485,033; 4,537,776; 4,637,930; 4,695,465.

Another example of delivery of the compounds and compositions of the invention for the treatment of epithelial injury is topical delivery, for example, in the form of oils and lotions. Topical delivery compositions are well known in the art, and described, for example, in U.S. Pat. Nos. 5,614,178; 7,241,456; and 5,720,948.

III. Methods of Treatment

In one aspect, the invention provides methods useful to overcome intestinal epithelial damage or injury due to ischemia, chemotherapy, radiation, or mechanical injury. The invention relates to the use of calcimimetics to inhibit apoptosis and/or necrosis and promote cell survival in subjects with epithelial injury. The epithelial tissue for which the methods of the present invention are contemplated, is, in one example, simple epithelium. In another example, it is stratified epithelium. In a further example, it is pseudostratified epithelium. In one aspect, the epithelial injury can be intestinal epithelial injury. In another aspect, it can be skin injury. In a further aspect, it can be the injury to the stratified squamous epithelium, e.g., the epithelium of the mouth, the esophagus, and the part of the rectum. In another aspect, it can be the injury to the squamous, columnar, or pseudostratified epithelial cells.

In one aspect, the invention relates to a method for treating subjects who are about to undergo chemotherapy, radiation therapy or surgery. In this aspect, a subject can be pre-treated with a calcimimetic compound of the invention prior to undergoing chemotherapy, radiation therapy or surgery. The example of a pre-treatment protocol is described below.

Another aspect of the invention relates to a method of treatment for subjects receiving cytotoxic agents such as biocides (e.g., anti-virals, anti-fungals and anti-bacterials) causing adverse effects on the GI tract. A further aspect of the invention deals with the epithelial injury caused by a disease, for example, osmotic diarrhea.

One aspect of the present invention can be applied to ameliorate the adverse effects due to chemical insult. Examples of application include inhibition or prevention of epithelial injury induced development of intestinal mucositis, reduction of the incidence and severity of infection, inhibition of white blood cell depletion, and damage resistance to the large bowel.

Another aspect of the present invention is to ameliorate the adverse effects of epithelial injury in the functioning of the small bowel, e.g., to improve the incidence of malabsorption, ulceration, bleeding, infection, diarrhea, fibrosis and stricture formation leading to reduced length and function of the bowel.

For use in pre-treating a subject in accordance with the present invention, the calcimimetics compound of the invention can be administered to the subject on a daily basis for a predetermined period of time prior to epithelial injury. Suitable pretreatment periods are identified as those providing a given benefit to the subject, relative to the subjects not pre-treated with a calcimimetic compound, in terms of any one of these endpoints following injury: enhanced survival, improved small or large bowel health or function, higher white blood cell count, reduced incidence of infection or bacterial count, and incidence of mucositis. In one aspect, the pre-treatment period consist of from one day to seven days. In one example, the pretreatment period consists of three consecutive days of pre-treatment with a calcimimetic composition in the doses described supra.

The invention further provides methods for treating epithelial injury due to mechanical stress, e.g., wound healing, skin grafting or surgery. All types of epithelial injury are contemplated to be treated in this aspect of the invention. In one aspect of the invention, the compounds and compositions of the inventions could be used to treat or pre-treat skin grafts to accelerate healing. The compounds of the invention can be used before, during, or after surgery to improve healing and prevent cell death.

Different markers of epithelial injury are known in the art. Clinical symptoms are most commonly used as a surrogate endpoint during and following treatment. Types of skin injury may include cuts, scrapes, bruises. UV damage markers are dry skin, sunburn or actinic keratosis. Symptoms of intestinal epithelial injury include anorexia, nausea, vomiting, mucosal injury, abdominal cramps and diarrhea. These symptoms may occur immediately following the injury. Often they manifest 2 or 2 weeks after the injury (for example, after chemotherapy or during radiation) and last 2-6 weeks following the injury. Assessment of mucosal transport and barrier function can be done through measuring absorption of test markers or test for nutrient malabsorption. See Lutgens L. et al. (2007) World J. Gastroenterol. 13(22): 3033-3042. Other biomarkers of intestinal epithelial injury include the plasma diamine oxidase (DAO) activity, for example, for measuring ischemic small bowel injury, fatty acid-binding proteins, calprotectin and citrulline. Additional biomarkers of the epithelial injury are described in more detail in Examples below.

The progress of the treatment as contemplated by the methods of the invention can be measured by observing the clinical symptoms or endpoints or evaluating suitable biomarkers for each individual type of injury before, during and after the treatment with the calcimimetic compounds and the compositions of the invention.

The following examples are offered to more fully illustrate the invention, but are not to be construed as limiting the scope thereof.

EXAMPLE 1

This example demonstrates that calcimimetic compounds protect ileal villi from ischemic injury.

Animals.

Male ($Casr^{+/+}$;$Gcm2^{-/-}$) or CaSR knockout ($Casr^{-/-}$; $Gcm2^{-/-}$) mice weighing 22-27 grams (upper panel) or male Sprague-Dawley rats weighing 220-275 grams (lower panel) were allowed free access to water and food prior to experimentation. The animals were exposed to an overdose of isofluorane and the ileum was removed. The ileum was then cut into 4 cm long sections and each section was placed in EDTA (20 mM) to isolate individual villi for 20 minutes at 37° C. After this digestion period the villi were placed in a HEPES-Ringer Solution that was bubbled with 100% $O_2$ and were kept in this solution at 4° C. until use. All mice were generated at Yale University from a breeding colony. Male Sprague-Dawley rats were purchased from Charles River Laboratories Inc. (Wilmington, Mass.). All animals were cared for according to the standard protocols of the Yale University Animal Care and Use Committee.

Chemical Reagents.

The HEPES-Ringer solution contained (in mmol/L): NaCl 125; KCl 5; $MgCl_2$ 0.5; HEPES 22, $CaCl_2$ 0.1 or 1.6; glucose 10, pH=7.4. The solution was bubbled with 100% $O_2$. FLUO-4 from Invitrogen (Seattle, Wash., USA) and stock solutions were prepared in dimethyl sulphoxide (DMSO).

Calcimimetic solutions (Compound A, 3-(2-chlorophenyl)-N-((1R)-1-(3-(methyloxy)phenyl)ethyl)-1-propanamine) and Compound B, N-((6-(methyloxy)-4'-(trifluoromethyl)-1,1'-biphenyl-3-yl)methyl)-1-phenylethanamine were formulated using DMSO. Final concentrations of DMSO never exceeded 0.1% (v/v). Preliminary experiments indicated that the vehicle did not alter any cell injury parameters or effected survival.

Ischemic Injury and Calcium Measurements

Following isolation individual villi were placed on coverslips and loaded with the calcium indicator dye FLUO4-AM (10 µM) (Invitrogen, Oregon USA) for 15 minutes. Following loading the villi were transferred to the stage of an inverted microscope where they were perfused with 37° C. HEPES Ringer solution that was bubbled with 100% $O_2$. After a 5 minute equilibration period to remove any de-esterified dye villi were exposed to a HEPES Ringer solution that had been bubbled with 100% $N_2$ while collecting images every 15 sec at 535 nm emission and 490 nm excitation. Images were recorded for 20-30 minutes using DIC optics at 60× Magnification with a Cooled CCD camera and Metamorph Image acquisition and analysis software.

Ischemic Injury and Trypan Blue.

Individual villi were transferred to the stage of an inverted microscope where they were perfused with 37° C. HEPES Ringer solution that was bubbled with 100% $O_2$. After the 5 minute equilibration period villi were exposed to a HEPES Ringer solution that had been bubbled with 100% $N_2$. In one series Trypan Blue a non membrane permeant dye used for assessment of membrane integrity was added to the bath (0.1 mM Trypan Blue concentration dissolved directly into the bath solution, either 100% $O_2$ or 100% $N_2$). Images were then recorded at sequential time points using DIC optics at 60× Magnification using a Cooled CCD camera and Metafluor Image acquisition and analysis software. Final data was acquired at 30 min from start of perfusion for all groups. The number of Trypan blue positive cells were counted and a number recorded for each villi under each condition.

Statistical Analysis.

Calcium Measurements and Ischemic Injury

The increase in intracellular $Ca^{2+}$ is plotted as arbitrary fluorescent units (AFU) with higher numbers of AFU representing an increase in intracellular $Ca^{2+}$. The data for each villi with a minimum of 7 cells per villi were then pooled and recorded. A numeric mean was then given for the summation of all the cellular data from each villi and from each animal. For the studies presented there were 7 cells per villi, 5 villi per animal and 5 animals in each group.

Trypan Blue Measurements and Ischemic Injury

After 30 minutes of exposure to each experimental solution the number of Trypan Blue positive cells was recorded from a blinded observer. The final number of positive cells for each villi was recorded. The data for each villi with a minimum of 7 cells per villi were then pooled and recorded. A numeric mean was then given for the summation of all the cellular data from each villi and from each animal. For the studies presented there were 7 cells per villi, 5 villi per animal and 5 animals in each group.

The results are summarized in FIG. 1 which illustrates the effect of a calcimimetic compound A on protection from ischemic injury in isolated ileal villi from a rat. Panel A shows a time course for changes in intracellular calcium (as measured by a video fluorescence imaging system and the calcium sensitive fluorescent indicator FLUO-4: increases in intracellular calcium are indicated by a larger fluorescence intensity) following exposure to 100% $N_2$ (ischemic injury), supra. Panel B is a summary of change in intracellular calcium in a ileal villus following $N_2$ exposure. There was a sustained increase in calcium of greater than 200% of the initial value which was indicative of cell injury and eventual cell death. Panel C illustrates the protective effect of a 5 min exposure to a calcimimetic (100 nM compound A) showing no increase in calcium in the presence of 100% $N_2$ thereby indicating that there was no ischemia. Panel D is a summary of the protective effect of a calcimimetic (100 nM compound A) on villi exposed to ischemic injury.

EXAMPLE 2

This example indicates that calcimimetic compounds protect colonic crypts from ischemia.

Animals.

Male ($Casr^{+/+}$;$Gcm2^{-/-}$) or CaSR knockout ($Casr^{-/-}$; $Gcm2^{-/-}$) mice weighing 22-27 grams or male Sprague-Dawley rats weighing 220-275 grams were allowed free access to water and food prior to experimentation. The animals were exposed to an overdose of isofluorane and the colon was removed. The colon was then cut into 4 cm long sections and each section was placed in EDTA (20 mM) to isolate individual crypts for 20 minutes at 37° C. After this digestion period the crypts were placed in in a HEPES-Ringer Solution that was bubbled with 100% $O_2$ and were kept in this solution at 4° C. until use. All mice were generated at Yale University from a breeding colony. Male Sprague-Dawley rats were purchased from Charles River Laboratories Inc. (Wilmington, Mass.). All animals were cared for according to the standard protocols of the Yale University Animal Care and Use Committee.

Chemical Reagents, Ischemic Injury and Calcium Measurements, Ischemic Injury and Trypan Blue, Statistical Analysis—See Example 1.

Figure 2:
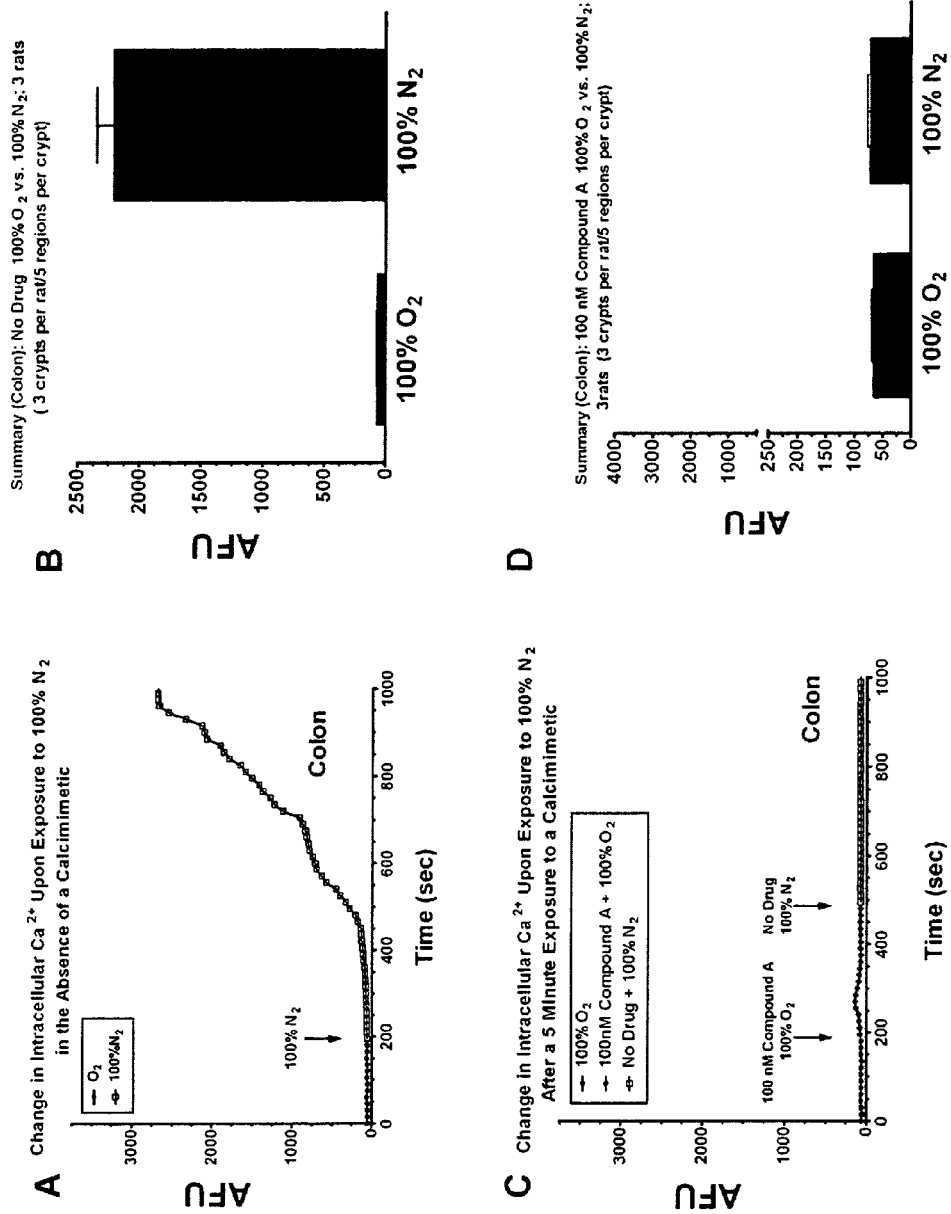
FIG. 2 demonstrates that calcimimetic compounds exhibit the protective effect against ischemia on rat colonic crypts. Panel A shows a time course for changes in intracellular calcium in a colonic crypt following exposure to 100% $N_2$ (ischemic injury). Panel B is a summary of change in intracellular calcium following $N_2$ exposure. Panel C illustrates the protective effect of a 5 min exposure to a calcimimetic (100 nM compound A) showing no increase in calcium in the presence of 100% $N_2$. Panel D is a summary of the protective effect of a calcimimetic (100 nM compound A) on colonic crypts exposed to ischemic injury.

The results are summarized in FIG. 2 which demonstrates that calcimimetic compounds exhibit the protective effect against ischemia on rat colonic crypts. Panel A shows a time course for changes in intracellular calcium in a colonic crypt following exposure to 100% $N_2$ (ischemic injury). Panel B is a summary of change in intracellular calcium following $N_2$ exposure. Panel C illustrates the protective effect of a 5 min exposure to a calcimimetic (100 nM compound A) showing no increase in calcium in the presence of 100% $N_2$. Panel D is a summary of the protective effect of a calcimimetic (100 nM compound A) on colonic crypts to exposed to ischemic injury. The five minute prepulse with 100 nM of compound A prevented the rise in intracellular calcium in the colonic crypt and thus extended the viability of the crypt in an oxygen free environment and prevented changes in the cell membrane (apoptosis).

EXAMPLE 3

Figure 3:
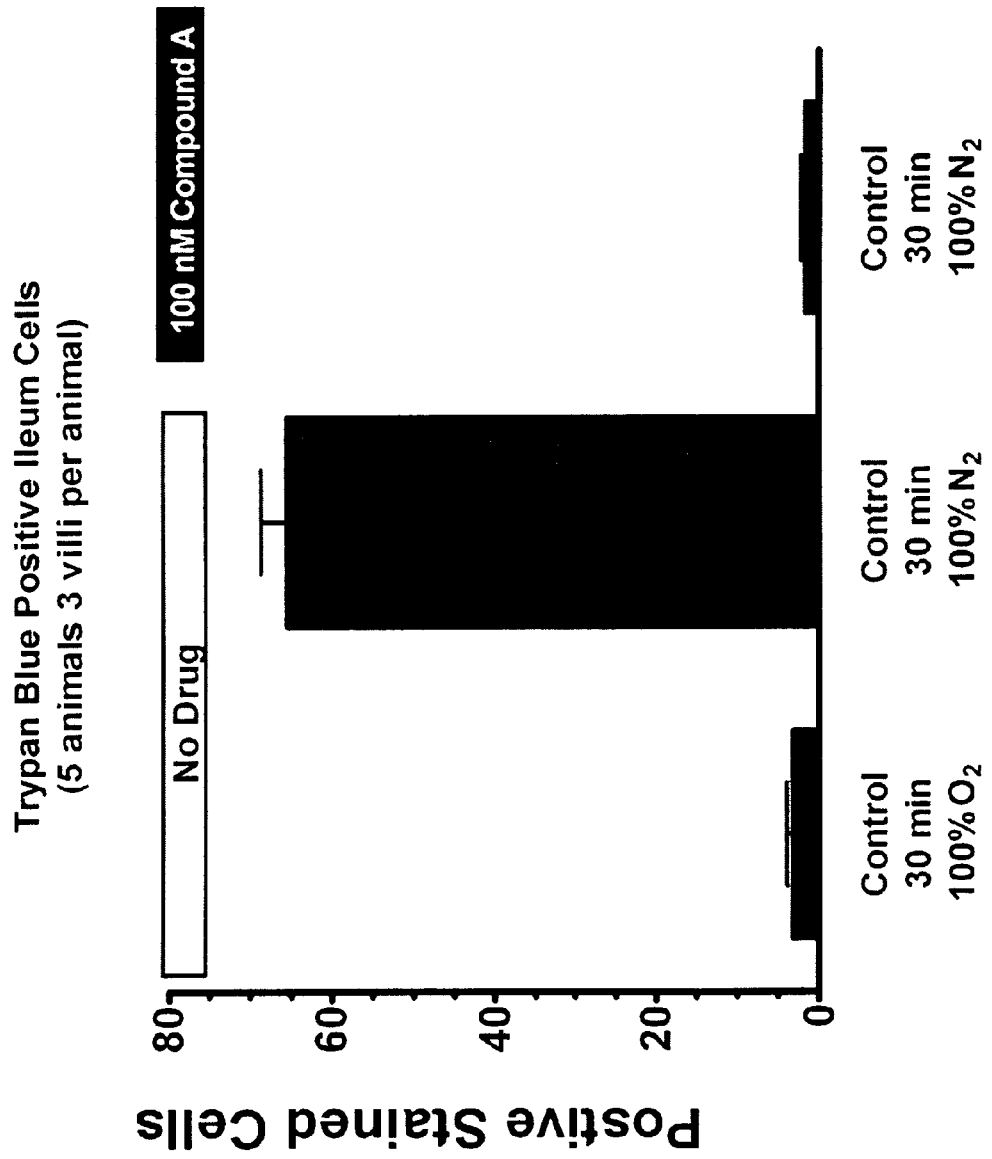
FIG. 3 illustrates the protective effect against cellular damage in rat ileal villi following a brief exposure to a calcimimetic by Trypan Blue Exclusion.

This example illustrates that calcimimetic can prevent cell death due to ischemia. FIG. 3 illustrates the protective effect against cellular damage in rat ileal villi following a brief exposure to a calcimimetic. Tissues were exposed to Trypan Blue, a diazo dye vital cellular stain used for assaying cellular damage and membrane integrity disruption. Live cells or cells without membrane damage were not stained. In the absence of a calcimimetic 30 minutes of exposure to ischemic conditions (100% $N_2$) resulted in greater than 60% cellular uptake of Trypan blue. Exposure to only 5 minutes of a 100 nM of a calcimimetic prevented uptake of Trypan Blue into ileal villi illustrating the protective effects of a calcimimetic (100 nM compound A) in preventing ischemic injury.

EXAMPLE 4

This example demonstrates the effects of calcimimetic treatment on wound injury and repair, the impact of Compound B on 96 genes implicated in wound injury, inflammation and repair were assessed in a mouse full-thickness cutaneous wound injury model. See Zoog S J et al. Cytometry A. (2009) March; 75(3): 189-98. The impact of calcimimetic treatment on gene mRNA biomarkers was assessed by quantitative PCR.

RNA Biomarkers for Wound Injury

For wound injury RNA biomarker exploration, female balb/c mice were randomly divided and treated with Compound B (3 mg/kg, n=5) or vehicle (20% Captisol in water, n=5) the day before cutaneous wounding and each subsequent day after until the termination of the studies. All mice received a 3 mm diameter full-thickness punch wound on day zero. On day 1 and day 3 post-injury, a 6 mm diameter skin biopsy was made over the original 3 mm wound and the wound tissue collected for RNA analysis. RNA was isolated using the Trizol reagent (Invitrogen) following manufacturer's instruction. 10 ng of total RNA was added to a single well at the final volume of 10 ul in 1×ABI (Applied Biosystems) Taqman qRT-PCR mixture and run on an ABI 7900 HT Real Time PCR system. For data analysis, the gene expression profile of each sample was first determined based on a control gene, Hprt1, using ABI SDS2.1 software. The signal of each sample was normalized further with Actb, Gapdh, Hprt1, and Rpl27. Genes showing differences between vehicle and a calcimimetic (Compound B) treated groups on days 1 and 3 are summarized in Table 2.

Calcimimetic treated mice showed an average plasma level of 20-36 ng/ml over the course of the study, and a corresponding reduction of serum total calcium level of 7.21-7.9 mg/dL compared to a total calcium level of 10.2-10.9 mg/dL in vehicle treated animals. These results suggest that calcimimetic compounds had a pharmacodynamic effect on blood serum calcium that may impact cutaneous wound injury, inflammation and repair responses.

Figure 4:
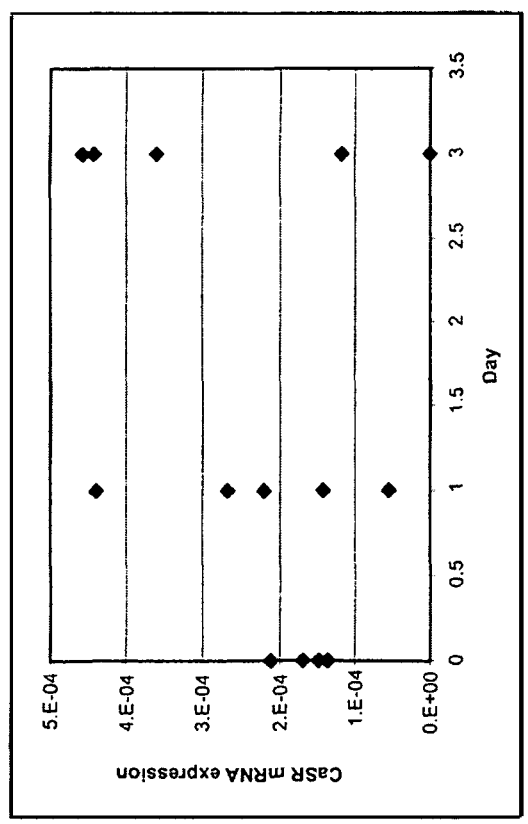
FIG. 4 illustrates CaSR RNA expression in normal and injured skin following the full-thickness wound on day 1 and day 3 post-injury. Calcium sensing receptor RNA is expressed as the % of control in calcimimetic (Compound B) treated animals on day 1 (D1) and day 3 (D3) post-injury, (n=4-5).

Biomarker gene RNA analysis showed that the CaSR is expressed in normal skin and in injured skin day 1 an day 3 post-injury in Compound B treated animals (FIG. 4). This suggests that the CaSR is expressed in wound tissue, and hence may be modulated by calcimimetics (FIG. 4).

The biomarkers of wound injury, inflammation and repair that were dynamically affected by Compound B on day 1 and day 3 compared to vehicle control are shown in Table 2. Calcimimetic Compound B affected inflammatory genes, and genes involved in remodeling and repair. Specifically, key inflammatory cytokines such as IL-1a and TNF that may promote cell death were affected by Compound B. Genes involved in inflammation and repair that were affected included: tryptase, TIMP-3, and MMP13. Genes involved in promoting cell survival included: VEGFa, TGFb1, eNOS, and PDGFRb. Immune cell related genes included: M-CSF, TLR-7 and CD3. Other relevant genes included: ITGA3 and PRG-1. Thus, calcimimetics demonstrated pharmacodynamic activity affecting wound biomarker gene expression in the cutaneous wound injury model. Table 2 represents the fold increase of drug-induced quantitative change in the gene over vehicle as determined by PCR analysis (n=5 in each drug or vehicle treated cohort).

TABLE 2

| Fold Increase (C/V) | Day 1 | Day 3 |
|---|---|---|
| VEGFa | 1.53 | 0.61 |
| IL-1a | 1.78 | 3.44 |
| M-CSF | 2.13 | 2.13 |
| TLR-7 | 2.20 | 2.39 |
| TNFR(p75) | 1.62 | 1.62 |
| TNFalpha | 1.26 | 3.83 |
| TGFB1 | 4.17 | 0.92 |
| ITGA3 | 4.89 | 1.78 |
| PRG-1 | 3.03 | 4.12 |
| MMP13 | 2.78 | 1.90 |
| TIMP-3 | 4.48 | 1.62 |
| eNOS | 5.41 | 0.46 |
| Tryptase b2 (MCP-6) | 1.02 | 0.95 |
| CD3 | 2.90 | 0.88 |
| PDGFRb(CD140) | 0.67 | 1.42 |

EXAMPLE 5

This example demonstrates a protective effect of the calcimimetic compounds in radiation injury in ileum.

Animals.

Male ($Casr^{+/+}$;$Gcm2^{-/-}$) or CaSR knockout ($Casr^{-/-}$; $Gcm2^{-/-}$) mice weighing 22-27 grams or male Sprague-Dawley rats weighing 220-275 grams were allowed free access to water and food prior to experimentation. The animals were exposed to an overdose of isofluorane and the ileum was removed. The ileum was then cut into 4 cm long sections and each section was to placed in EDTA (20 mM) to isolate individual villi for 20 minutes at 37° C. After this digestion period the villi were placed in a HEPES-Ringer Solution that was bubbled with 100% $O_2$ and were kept in this solution at 4° C. until use. All mice were generated at Yale University from a breeding colony. Male Spraque-Dawley rats were purchased from Charles River Laboratories Inc. (Wilmington, Mass.). All animals were cared for according to the standard protocols of the Yale University Animal Care and Use Committee.

Chemical Reagents.

The HEPES-Ringer solution contained (in mmol/L): NaCl 125; KCl 5; $MgCl_2$ 0.5; HEPES 22, $CaCl_2$ 0.1 or 1.6; glucose 10, pH=7.4. The solution was bubbled with 100% $O_2$. Live Dead Assay (Invitrogen OR) Live cells are distinguished by the presence of ubiquitous intracellular esterase activity, determined by the enzymatic conversion of the virtually non-fluorescent cell-permeant calcein AM to the intensely fluorescent calcein. The polyanionic dye calcein was well retained within live cells, producing an intense uniform green fluorescence in live cells (ex/em ~495 nm/~515 nm). EthD-1 entered cells with damaged membranes and underwent a 40-fold enhancement of fluorescence upon binding to nucleic acids, thereby producing a bright red fluorescence in dead cells (ex/em ~495 nm/~635 nm). EthD-1 was excluded by the intact plasma membrane of live cells. The determination of cell viability depended on these physical and biochemical properties of cells. Background fluorescence levels were inherently low with this assay technique because the dyes were virtually non-fluorescent before interacting with cells.

Radiation Injury and Live Dead Assay Measurements

Following isolation individual villi were placed on cover slips and transferred to the stage of an inverted microscope where they were perfused with 37° C. HEPES Ringer solution that was bubbled with 100% $O_2$. After a 5 minute equilibration period villi were exposed to UV A and UV B radiation delivered from a 300 W Xenon Source. The radiation was focused on the individual villi for a 20 min exposure period while continually perfusing the chamber with HEPES Ringer solution that had been bubbled with 100% $O_2$. At the end of this period in one series, Images were recorded using the Metafluor image acquisition program and analysis software. An independent observer counted the number of dead cells per villi. This process was repeated for each animal and the numbers were then pooled for statistical analysis.

Radiation Injury and Trypan Blue.

Individual villi were transferred to the stage of an inverted microscope where they were perfused with 37° C. HEPES Ringer solution that was bubbled with 100% $O_2$. After a 5 minute equilibration period villi were exposed to UV A and UV B radiation delivered from a 300 W Xenon Source. The radiation was focused on the individual villi for a 20 min exposure period while continually perfusing the chamber with HEPES Ringer solution that had been bubbled with 100% $O_2$. In one series Trypan Blue a non membrane permeant dye used for assessment of membrane integrity was added to the bath (0.1 mM Trypan Blue concentration dissolved directly into the bath solution). Images were then recorded at sequential time points using DIC optics at 60× Magnification using a Cooled CCD camera and Metafluor Image acquisition and analysis software. Final data was acquired at 30 min from start of perfusion for all groups. The number of Trypan blue positive cells were counted and a number recorded for each villi under each condition.

Statistical Analysis.

Live Dead Measurements and Radiation Injury

The increase in cells staining positive for the dead assay ethidium homodimer (EthD-1) was plotted as dead cells. The data for each villi with a minimum of 7 cells per villi were then pooled and recorded. A numeric mean was then given for the summation of all the cellular data from each villi and from each animal. For the studies presented there were 7 cells per villi, 5 villi per animal and 5 animals in each group.

Trypan Blue Measurements and Radiation Injury

After 30 minutes of exposure to each experimental solution the number of Trypan Blue positive cells was recorded from a blinded observer. The final number of positive cells for each villi was recorded. The data for each villi with a minimum of 7 cells per villi were then pooled and recorded. A numeric mean was then given for the summation of all the cellular data from each villi and from each animal. For the studies presented there were 7 cells per villi, 5 villi per animal and 5 animals in each group.

Figure 5:
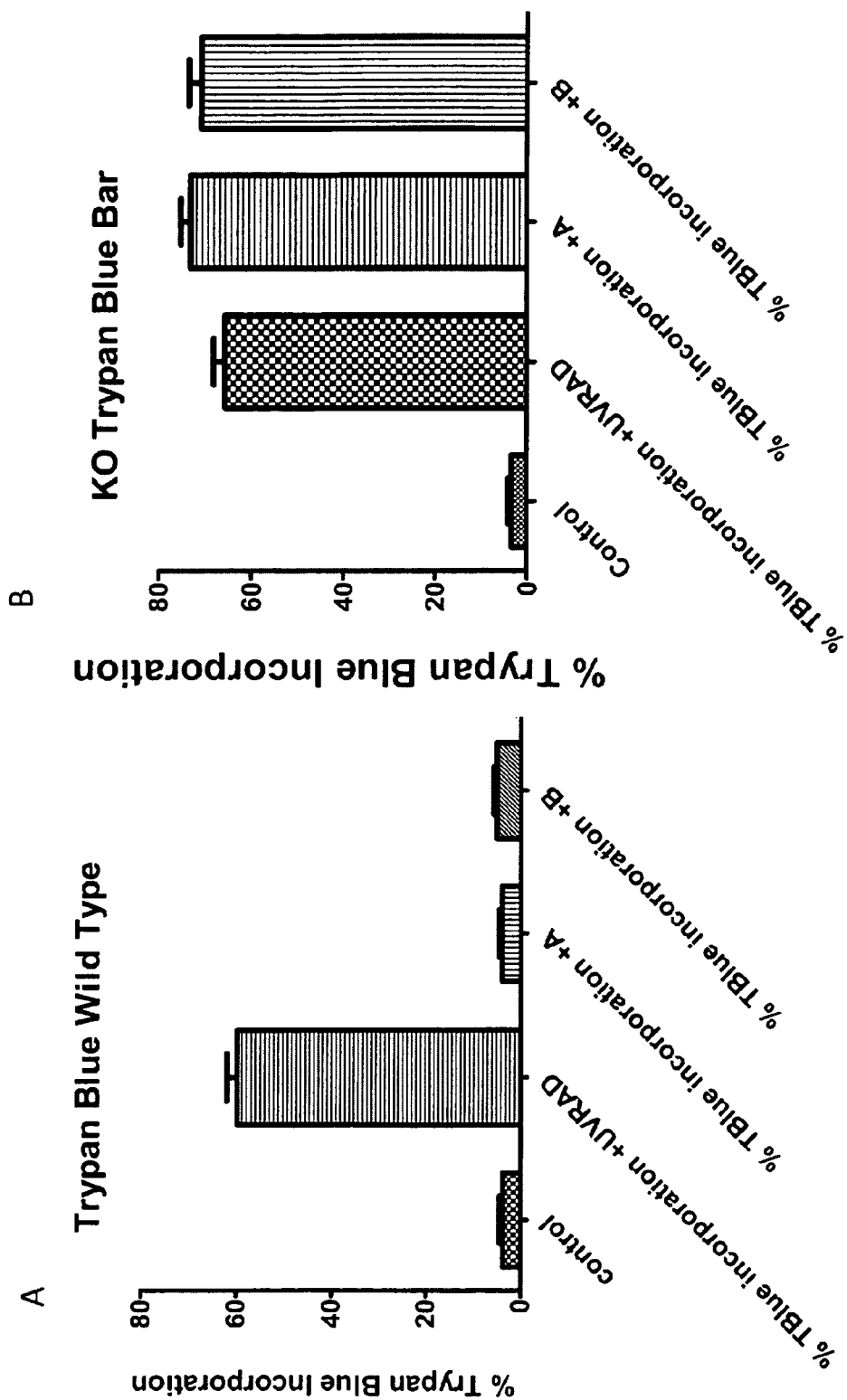
FIG. 5 illustrates the effect of radiation injury on ileal function. Panel A is a composite summary plot of effects of UVA and UVB radiation on mouse ileal villi cell integrity in the presence and absence of a calcimimetic. Panel B is a composite summary plot of the effects of UVA and UVB radiation on CaSR knockout mouse cell integrity in the presence and absence of a calcimimetic.

The results are presented in FIG. 5, which summarizes the effect of radiation injury on the ileal function. Panel A is a composite summary plot of effects of UVA and UVB radiation on mouse ileal villi cell integrity in the presence and absence of a calcimimetic. The calcimimetic prevents Trypan blue uptake thereby showing improved cell health. Panel B is a composite summary plot of the effects of UVA and UVB radiation on CaSR knockout mouse cell integrity in the presence and absence of a calcimimetic. The calcimimetic has no effect on preventing Trypan blue uptake thereby showing the protective effect of the calcimimetic is linked to functional calcium sensing receptor in the ileum.

EXAMPLE 6

This example demonstrates a protective effect of the calcimimetic compounds in radiation injury in ileum.

Animals.

Male ($Casr^{+/+}$;$Gcm2^{-/-}$) or CaSR knockout ($Casr^{-/-}$; $Gcm2^{-/-}$) mice weighing 22-27 grams or male Sprague-Dawley rats weighing 220-275 grams were allowed free access to water and food prior to experimentation. The animals were exposed to an overdose of isofluorane and the ileum was removed. The colon was then cut into 4 cm long sections and each section was placed in EDTA (20 mM) to isolate individual crypts for 20 minutes at 37° C. After this digestion period the crypts were placed in a HEPES-Ringer Solution that was bubbled with 100% $O_2$ and were kept in this solution at 4° C. until use. All mice were generated at Yale University from a breeding colony. Male Spraque-Dawley rats were purchased from Charles River Laboratories Inc. (Wilmington, Mass.). All animals were cared for according to the standard protocols of the Yale University Animal Care and Use Committee.

Chemical Reagents.

The HEPES-Ringer solution contained (in mmol/L): NaCl 125; KCl 5; $MgCl_2$ 0.5; HEPES 22, $CaCl_2$ 0.1 or 1.6; glucose 10, pH=7.4. The solution was bubbled with 100% $O_2$. Live Dead Assay (Invitrogen, OR) Live cells are distinguished by the presence of ubiquitous intracellular esterase activity, determined by the enzymatic conversion of the virtually non-fluorescent cell-permeant calcein AM to the intensely fluorescent calcein. The polyanionic dye calcein was well retained within live cells, producing an intense uniform green fluorescence in live cells (ex/em ~495 nm/~515 nm). EthD-1 entered cells with damaged membranes and underwent a 40-fold enhancement of fluorescence upon binding to nucleic acids, thereby producing a bright red fluorescence in dead cells (ex/em ~495 nm/~635 nm). EthD-1 was excluded by the intact plasma membrane of live cells. The determination of cell viability depended on these physical and biochemical properties of cells. Background fluorescence levels were inherently low with this assay technique because the dyes were virtually non-fluorescent before interacting with cells.

Radiation Injury and Live Dead Assay Measurements

Following isolation individual crypts were placed on cover slips and transferred to the stage of an inverted microscope where they were perfused with 37° C. HEPES Ringer solution that was bubbled with 100% $O_2$. After a 5 minute equilibration period crypts were exposed to UV A and UV B radiation delivered from a 300 W Xenon Source. The radiation was focused on the individual crypts for a 20 min exposure period while continually perfusing the chamber with HEPES Ringer solution that had been bubbled with 100% $O_2$. At the end of this period in one series, Images were recorded using the Metafluor image acquisition program and analysis software. An independent observer counted the number of dead cells per crypts. This process was repeated for each animal and the numbers were then pooled for statistical analysis.

Radiation Injury and Trypan Blue.

Individual crypts were transferred to the stage of an inverted microscope where they were perfused with 37° C. HEPES Ringer solution that was bubbled with 100% $O_2$. After a 5 minute equilibration period crypts were exposed to UV A and UV B radiation delivered from a 300 W Xenon Source. The radiation was focused on the individual crypts for a 20 min exposure period while continually perfusing the chamber with HEPES Ringer solution that had been bubbled with 100% $O_2$. In one series Trypan Blue a non membrane permeant dye used for assessment of membrane integrity was added to the bath (0.1 mM Trypan Blue concentration dissolved directly into the bath solution). Images were then recorded at sequential time points using DIC optics at 60× Magnification using a Cooled CCD camera and Metafluor Image acquisition and analysis software. Final data was acquired at 30 min from start of perfusion for all groups. The number of Trypan blue positive cells were counted and a number recorded for each villi under each condition.

Statistical Analysis.

Live Dead Measurements and Radiation Injury

The increase in cells staining positive for the dead assay ethidium homodimer (EthD-1) is plotted as dead cells. The data for each crypt with a minimum of 7 cells per villi were then pooled and recorded. A numeric mean was then given for the summation of all the cellular data from each crypts and from each animal. For the studies presented there were 7 cells per crypts, 5 crypts per animal and 5 animals in each group.

Trypan Blue Measurements and Radiation Injury

After 30 minutes of exposure to each experimental solution the number of Trypan Blue positive cells was recorded from a blinded observer. The final number of positive cells for each crypts was recorded. The data for each crypts with a minimum of 7 cells per crypts were then pooled and recorded. A numeric mean was then given for the summation of all the cellular data from each crypt and from each animal. For the studies presented there were 7 cells per crypts, 5 crypts per animal and 5 animals in each group.

Figure 6:
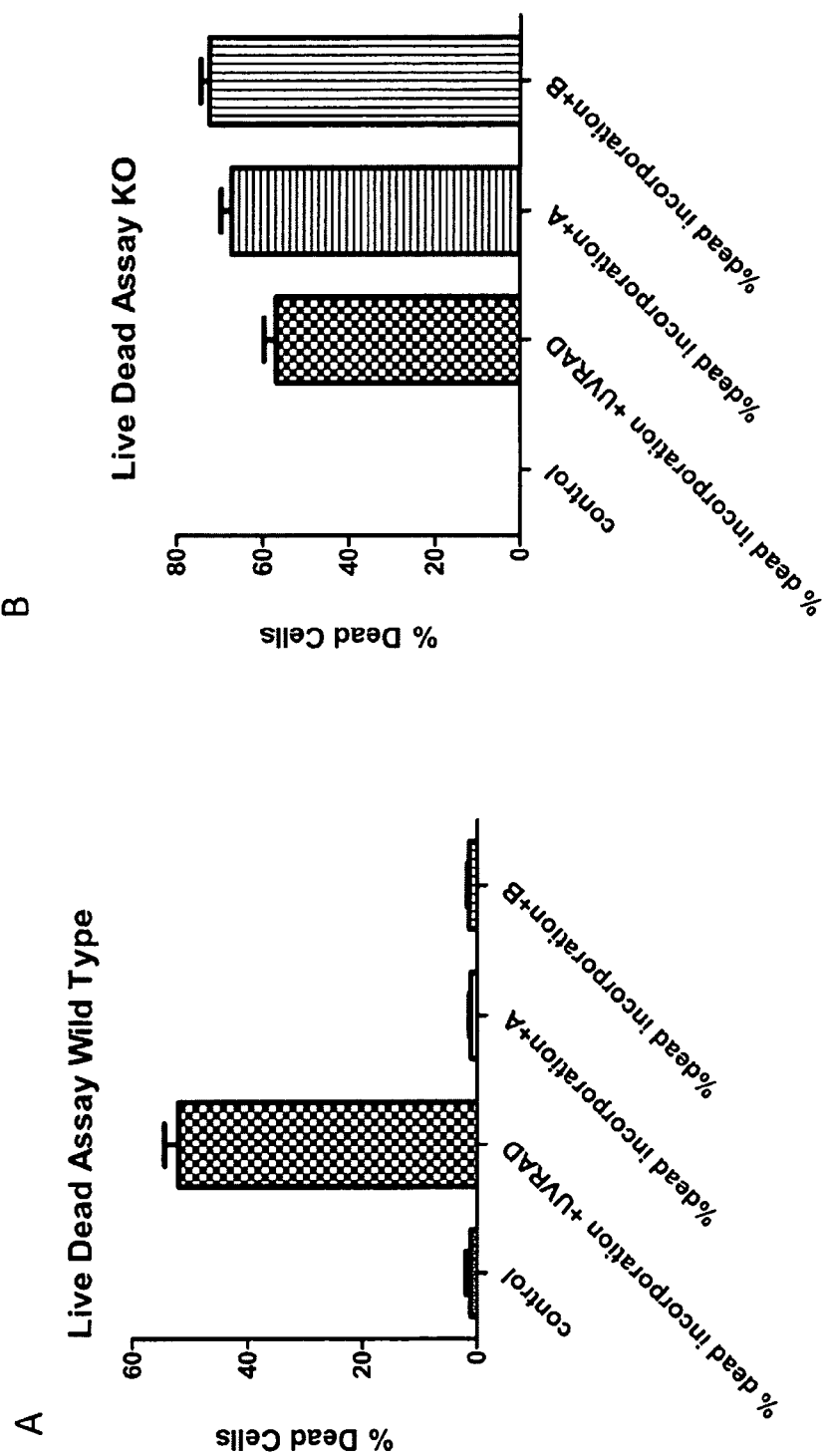
FIG. 6 demonstrates the effect of radiation injury on colonic function. Panel A is a composite summary plot of effects of UVA and UVB radiation on mouse colonic crypt cell integrity in the presence and absence of a calcimimetic. Panel B is a composite summary plot of the effects of UVA and UVB radiation on CaSR knockout mouse cell integrity in the presence and absence of a calcimimetic.

The results are summarized in FIG. 6, which illustrates the effect of radiation injury on the colonic function. Panel A is a composite summary plot of effects of UVA and UVB radiation on mouse colonic crypt cell integrity in the presence and absence of a calcimimetic. The calcimimetic prevents Trypan blue uptake thereby showing improved cell health. Panel B is a composite summary plot of the effects of UVA and UVB radiation on CaSR knockout mouse cell integrity in the presence and absence of a calcimimetic. The calcimimetic has no effect on preventing Trypan blue uptake thereby showing the protective effect of the calcimimetic is linked to functional calcium sensing receptor in the colon.

EXAMPLE 7

This example demonstrates that calcimimetic compounds exhibit a protective effect against radiation injury in ileum.

Animals.

Male ($Casr^{+/+}$;$Gcm2^{-/-}$) or CaSR knockout ($Casr^{-/-}$; $Gcm2^{-/-}$) mice weighing 22-27 grams or male Sprague-Dawley rats weighing 220-275 were allowed free access to water and food prior to experimentation. The animals were exposed to an overdose of isofluorane and the ileum was removed. The ileum was then cut into 4 cm long sections and each section was placed in EDTA (20 mM) to isolate individual villi for 20 minutes at 37° C. After this digestion period the villi were placed in a HEPES-Ringer Solution that was bubbled with 100% $O_2$ and were kept in this solution at 4° C. until use. All mice were generated at Yale University from a breeding colony. Male Sprague-Dawley rats were purchased from Charles River Laboratories Inc. (Wilmington, Mass.). All animals were cared for according to the standard protocols of the Yale University Animal Care and Use Committee.

Chemical Injury and Cell Volume Change

Following isolation individual villi were placed on cover slips and transferred to the stage of an inverted microscope where they were perfused with 37° C. HEPES Ringer solution that was bubbled with 100% $O_2$. After a 5 minute equilibration period villi were exposed to a standard HEPES-Ringer Solution+50 mM Sorbitol. Images were recorded using the Metamorph image acquisition program and analysis software every 15 seconds following exposure to Sorbitol. An independent observer measured villi diameter at the beginning and during each subsequent time period for a total of 15 minutes. This process was repeated for each animal and the numbers were then pooled for statistical analysis.

Statistical Analysis.

Cell Volume Measurements and Chemical Injury: the increase in cells staining positive for the dead assay ethidium homodimer (EthD-1) was plotted as dead cells. The data for each villi were recorded. A numeric mean was then given for the summation of all the villi volume data from each villi and from each animal. For the studies presented there were 5 villi per animal and 5 animals in each group.

Figure 7:
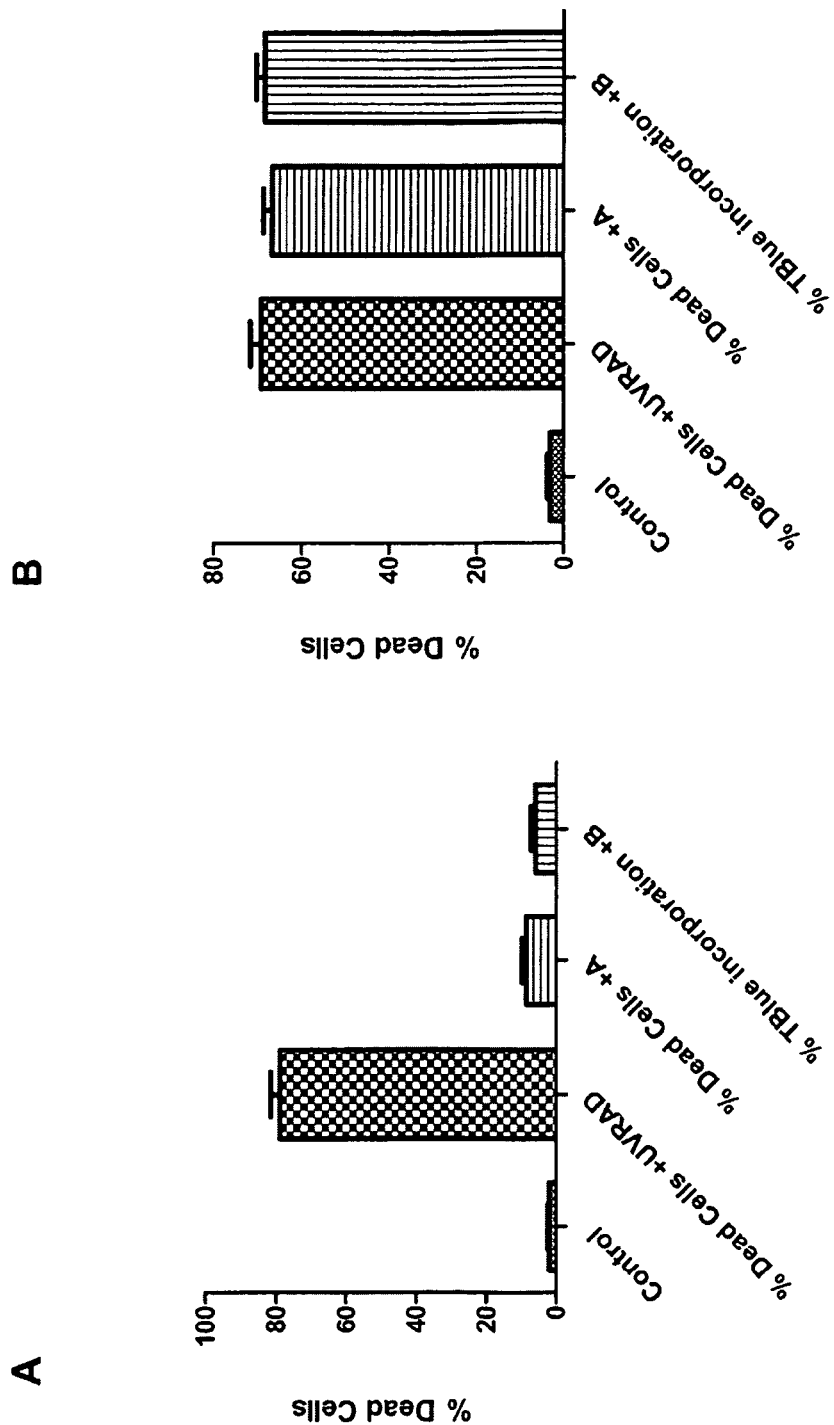
FIG. 7 illustrates the effect of radiation injury on the ileal function. Panel A is a composite summary plot of effects of UVA and UVB radiation on mouse ileal villi cell integrity in the presence and absence of a calcimimetic. Panel B is a composite summary plot of the effects of UVA and UVB radiation on CaSR knockout mouse cell integrity in the presence and absence of a calcimimetic.

The results are presented in FIG. 7, which depicts the effect of radiation injury on the ileal function. Panel A is a composite summary plot of effects of UVA and UVB radiation on mouse ileal villi cell integrity in the presence and absence of a calcimimetic. The calcimimetic prevents increase in uptake of the ethidium homodimer thereby showing improved cell health. Panel B is a composite summary plot of the effects of UVA and UVB radiation on CaSR knockout mouse cell integrity in the presence and absence of a calcimimetic. The calcimimetic has no effect on preventing ethidium homodimer uptake thereby showing the protective effect of the calcimimetic is linked to functional calcium sensing receptor in the ileum.

EXAMPLE 8

This example demonstrates that calcimimetic compounds exhibit a protective effect against chemical injury in colon.

Figure 8:
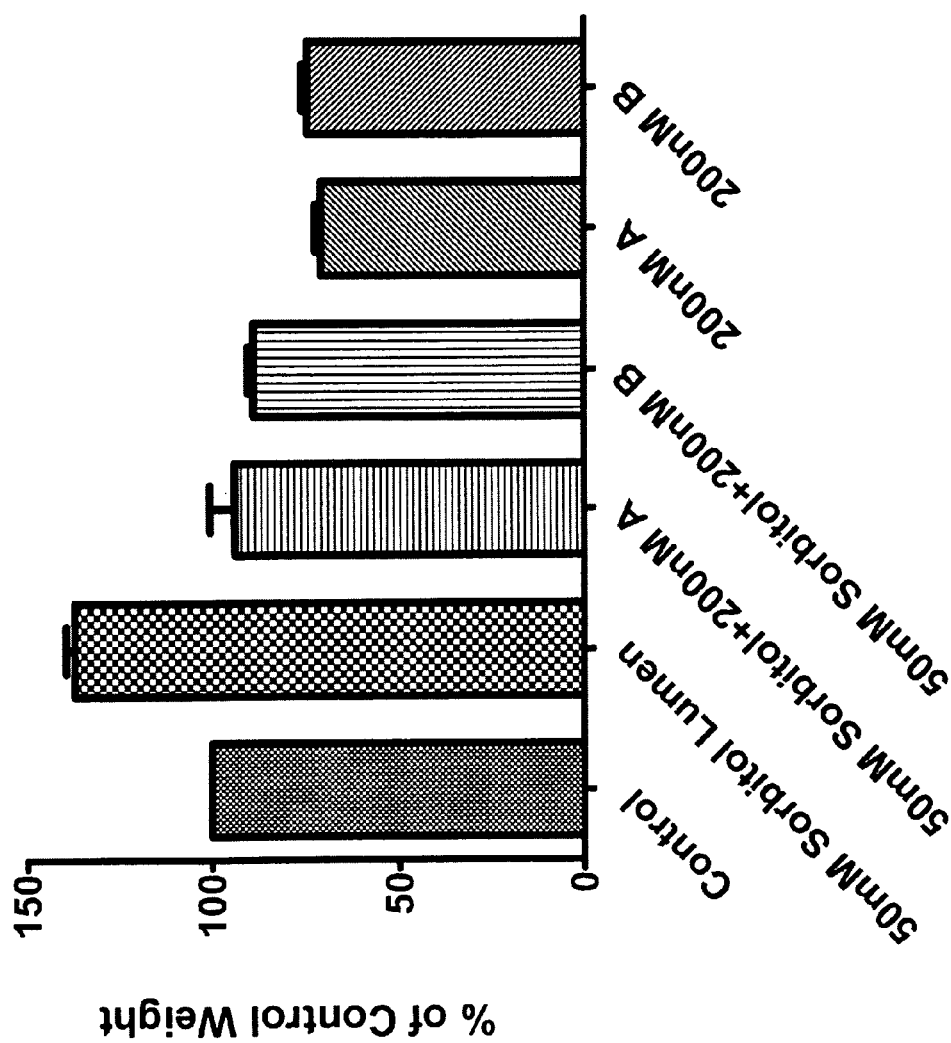
FIG. 8 demonstrates the effect of chemical injury on the ileal function. Summary graph shows the effects of a chemical injury from 50 mM Sorbitol on ileum sections in the presence and absence of a calcimimetic.

The results are presented in FIG. 8 summarizing the effect of chemical injury on the ileal function. Summary graph shows the effects of a chemical injury from 50 mM Sorbitol on Ileum sections in the presence and absence of a calcimimetic. Exposure to Sorbitol leads to an increase in tissue weight due to injury. In the presence of a calcimimetic there is no change in weight indicative of protection from a chemical injury.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for treating gastrointestinal epithelial injury induced by hypoxia or ischemia comprising administering to a subject in need thereof, wherein the subject does not have a diarrhea, a therapeutically effective amount of a calcimimetic compound of Formula I

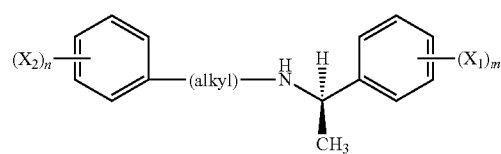

wherein:

$X_1$ and $X_2$, which may be identical or different, are each a radical chosen from $CH_3$, $CH_3O$, $CH_3CH_2O$, Br, Cl, F, $CF_3$, $CHF_2$, $CH_2F$, $CF_3O$, $CH_3S$, OH, $CH_2OH$, $CONH_2$, CN, $NO_2$, $CH_3CH_2$, propyl, isopropyl, butyl, isobutyl, t-butyl, acetoxy, and acetyl radicals, or two of $X_1$ may together form an entity chosen from fused cycloaliphatic rings, fused aromatic rings, and a methylene doxy radical, or two of $X_2$ may together form an entity chosen from fused cycloaliphatic rings, fused aromatic rings, and a methylene dioxy radical; provided that $X_2$ is not a 3-t-butyl radical;

n ranges from 0 to 5;

m ranges from 1 to 5; and the alkyl radical is chosen from $C_1$-$C_3$ alkyl radicals, which are optionally substituted with at least one group chosen from saturated and unsaturated, linear, branched, and cyclic $C_1$-$C_9$ alkyl groups, dihydroindolyl and thiodihydroindolyl groups, and 2-, 3-, and 4-piperidinyl groups;

or a pharmaceutically acceptable salt thereof.

2. The method of claim 1, wherein the calcimimetic compound is N-(3[2-chlorophertyl]-propyl)-R-χ-methyl-3-methoxybenzylamine or a pharmaceutically acceptable salt thereof.

3. The method of claim 1, wherein the calcimimetic compounds is cinacalcet HCl.

4. The method of claim 1, wherein the subject is a mammal.

5. The method of claim 1, wherein the subject is human.

\* \* \* \* \*

UNITED STATES PATENT AND TRADEMARK OFFICE
CERTIFICATE OF CORRECTION

PATENT NO.       : 8,609,655 B2                           Page 1 of 1
APPLICATION NO. : 12/935263
DATED            : December 17, 2013
INVENTOR(S)      : Geibel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 295 days.

Signed and Sealed this
Twenty-second Day of September, 2015

Michelle K. Lee
*Director of the United States Patent and Trademark Office*